United States Patent
Newbold et al.

(10) Patent No.: US 11,906,402 B2
(45) Date of Patent: Feb. 20, 2024

(54) AUTOMATIC ASEPTIC SAMPLING VALVE FOR SAMPLING FROM ENCLOSED CONTAINERS

(71) Applicant: EMD Millipore Corporation, Burlington, MA (US)

(72) Inventors: David D. Newbold, Bend, OR (US); Douglas L. Millard, Bend, OR (US); Erwin Y. Yu, Ballwin, MO (US); Paul T. Jeffers, Frankfield (IE); Jeffrey W. Weber, Portage, MI (US)

(73) Assignee: EMD Millipore Corporation, Burlington, MA (US)

( * ) Notice: Subject to any disclaimer, the term of this patent is extended or adjusted under 35 U.S.C. 154(b) by 515 days.

(21) Appl. No.: 15/356,331

(22) Filed: Nov. 18, 2016

(65) Prior Publication Data

US 2017/0067801 A1    Mar. 9, 2017

Related U.S. Application Data

(63) Continuation of application No. 14/116,123, filed as application No. PCT/US2012/036652 on May 4, 2012, now Pat. No. 9,499,782.
(Continued)

(51) Int. Cl.
*G01N 1/20* (2006.01)
*G01N 1/14* (2006.01)
(Continued)

(52) U.S. Cl.
CPC ........... *G01N 1/2035* (2013.01); *C12M 33/04* (2013.01); *C12M 37/00* (2013.01); *G01N 1/10* (2013.01); *G01N 1/14* (2013.01); *G01N 1/20* (2013.01); *G01N 2001/1445* (2013.01); *G01N 2001/205* (2013.01)

(58) Field of Classification Search
CPC ................................................ G01N 2001/205
See application file for complete search history.

(56) References Cited

U.S. PATENT DOCUMENTS 1,605,824 A * 11/1926 Erickson ............. F16K 31/0679
                                                              236/75
2,835,598 A *  5/1958 Kolner ................. B01D 9/0013
                                                              62/540
(Continued)

FOREIGN PATENT DOCUMENTS

| FR | 2617286 | 12/1988 |
|---|---|---|
| WO | WO 2006/086489 | 8/2006 |
| WO | WO 2011/038008 | 3/2011 |

OTHER PUBLICATIONS

Benz. "Bioreactor Designs for Chemical Engineers" Chem. Eng. Progress 107.8 (2011): 21-26.
(Continued)

*Primary Examiner* — Jamel E Williams
*Assistant Examiner* — Alex T Devito
(74) *Attorney, Agent, or Firm* — EMD Millipore Corporation

(57) ABSTRACT

A sample can be collected from an enclosed container by opening a sample collection valve and drawing the sample from the enclosed container. After delivery of the sample out of a fluid flow path, a sanitizing fluid can be directed along the fluid flow path to sanitize the fluid flow path.

10 Claims, 22 Drawing Sheets

Related U.S. Application Data

(60) Provisional application No. 61/584,189, filed on Jan. 6, 2012, provisional application No. 61/488,627, filed on May 20, 2011, provisional application No. 61/483,559, filed on May 6, 2011.

(51) Int. Cl.
- *C12M 1/26* (2006.01)
- *G01N 1/10* (2006.01)
- *C12M 1/12* (2006.01)

(56) References Cited

U.S. PATENT DOCUMENTS

| | | | |
|---|---|---|---|
| 3,379,216 | A | 4/1968 | Mercier |
| 3,713,988 | A | 1/1973 | Dawson et al. |
| 3,741,687 | A | 6/1973 | Nystroem |
| 3,771,562 | A | 11/1973 | Curran |
| 3,807,906 | A | 4/1974 | Breit |
| 4,121,619 | A | 10/1978 | Pauliukonis |
| 4,347,877 | A | 9/1982 | Hoiss |
| 4,548,088 | A | 10/1985 | Hood, Jr. |
| 4,889,812 | A | 12/1989 | Guinn et al. |
| 4,918,019 | A | 4/1990 | Guinn |
| 5,075,905 | A | 12/1991 | Rutherford |
| 5,131,226 | A | 7/1992 | Hendry |
| 5,296,197 | A | 3/1994 | Newberg et al. |
| 5,606,138 | A * | 2/1997 | Saarenketo .............. G01N 1/14 73/864.34 |
| 5,630,935 | A | 5/1997 | Treu |
| 5,948,998 | A | 9/1999 | Witte et al. |
| 6,085,602 | A | 7/2000 | Schorn et al. |
| 6,133,022 | A | 10/2000 | Newberg |
| 6,423,548 | B1 | 7/2002 | Newberg et al. |
| 6,491,283 | B2 | 12/2002 | Newberg |
| 6,516,677 | B1 | 2/2003 | Suter |
| 6,637,277 | B2 | 10/2003 | Gamache |
| 6,821,773 | B1 | 11/2004 | Newberg |
| 7,192,003 | B2 | 3/2007 | Hoobyar et al. |
| 7,389,792 | B2 | 6/2008 | Newburg |
| 7,601,545 | B2 | 10/2009 | Barringer, Jr. |
| 7,955,843 | B2 | 6/2011 | Barringer, Jr. |
| 8,549,934 | B2 | 10/2013 | Biksacky |
| 10,421,939 | B2 | 9/2019 | Ray et al. |
| 2002/0036017 | A1 | 3/2002 | Leys et al. |
| 2003/0027225 | A1 * | 2/2003 | Wada ................ G01N 27/44791 435/287.2 |
| 2004/0259241 | A1 | 12/2004 | Barringer, Jr. |
| 2005/0158701 | A1 | 7/2005 | West |
| 2005/0187532 | A1 | 8/2005 | Thurau et al. |
| 2007/0039653 | A1 | 2/2007 | Maggard |
| 2007/0128087 | A1 | 6/2007 | Cannizzaro et al. |
| 2007/0131289 | A1 | 6/2007 | Pataki |
| 2008/0032380 | A1 | 2/2008 | Kleis et al. |
| 2008/0134804 | A1 * | 6/2008 | Maeda ................ G01N 35/1097 73/863.01 |
| 2008/0289437 | A1 | 11/2008 | Saegusa |
| 2008/0308494 | A1 * | 12/2008 | Barringer, Jr. ........... G01N 1/14 210/636 |
| 2008/0314450 | A1 | 12/2008 | Hawker et al. |
| 2009/0038419 | A1 | 2/2009 | Hiller et al. |
| 2009/0068032 | A1 | 3/2009 | Furey |
| 2009/0178495 | A1 | 7/2009 | Steigmiller et al. |
| 2009/0199904 | A1 | 8/2009 | Babbitt et al. |
| 2010/0043883 | A1 | 2/2010 | Yu et al. |
| 2010/0047122 | A1 | 2/2010 | Barringer, Jr. |
| 2010/0102008 | A1 | 4/2010 | Hedberg |
| 2010/0236340 | A1 | 9/2010 | Lee et al. |
| 2011/0236990 | A1 | 9/2011 | Mizutani et al. |
| 2014/0087413 | A1 | 3/2014 | Newbold et al. |

OTHER PUBLICATIONS

Daken Stainless Products: "Keofitt W15 Sample Valves", (Jan. 1, 2005), Available at http://www.keofitt-uk.com/865541.htm [last accessed Nov. 17, 2016].

* cited by examiner

Assembly

Assembly

Liquid Side

Liquid Side

Air Side

Air Side

Air Side

AUTOMATIC ASEPTIC SAMPLING VALVE FOR SAMPLING FROM ENCLOSED CONTAINERS

CROSS REFERENCE TO RELATED APPLICATIONS

This application is a continuation of U.S. application Ser. No. 14/116,123, which was filed on Nov. 6, 2013, which is the U.S. National Stage of International Application No. PCT/US2012/036652, filed May 4, 2012, which was published in English under PCT Article 21(2), which in turn claims the benefit of U.S. Provisional Patent Application No. 61/483,559, filed on May 6, 2011, U.S. Provisional Patent Application No. 61/488,627, filed on May 20, 2011, and U.S. Provisional Patent Application No. 61/584,189, filed on Jan. 6, 2012, each of which are incorporated herein by reference in their entirety.

FIELD

The present disclosure is directed to an automatic aseptic sampling valve and methods of using the same.

BACKGROUND

Obtaining samples from containers or other systems that support biologically and/or chemically active environments can require complex and careful sampling procedures to avoid contamination of the containers or the environment itself. For example, most bioreactors require frequent sampling (e.g., one or more times a day) to monitor and control the conditions and levels of nutrients needed for cell growth. To reduce the risk of contamination within such systems, conventional sampling techniques generally require operators to perform multiple, labor-intensive steps.

SUMMARY

In some embodiments, the sampling systems and methods disclosed herein provide consistent sampling procedures for obtaining samples of a desired quality, while reducing the risk of contamination of the bioreactor and the need for labor-intensive operator attention.

A sampling system for collecting a fluid sample from an enclosed container is provided. The system can include (a) a sanitizing fluid inlet valve operable between an open position and a closed position; (b) a gas inlet valve operable between an open position and a closed position; (c) a sample collection valve operable between an open position and a closed position; (d) an outlet valve operable between an open position and a closed position; (e) a variable volume reservoir; and (f) a fluid flow path interconnecting (a)-(e). When (a), (b), and (d) are in the closed position, (c) can be in the open position to withdraw a sample from the enclosed container into the reservoir along a first portion of the fluid flow path. When (a), (b), and (c) are in the closed position, the sample can be discharged from the reservoir along a second portion of the fluid flow path through (d). When (a) is in the open position and (b) and (c) are in the closed position, a sanitizing fluid can be introduced into the fluid flow path through (a) to sanitize at least the first portion of the fluid flow path.

In some embodiments, when (a) is in the open position, and (b) and (c) are in the closed position, the sanitizing fluid also sanitizes the reservoir. In other embodiments, (a) is at an upstream portion of the fluid flow path and (d) is at a downstream portion of the fluid flow path, and the sanitizing fluid can flow through the fluid flow path from (a) to (d) to sanitize the fluid flow path between (a) and (d). In other embodiments, (a)-(e) are interconnected along the fluid flow path from the upstream portion to the downstream portion in the following order: (a), (b), (c), (e), and (d). The reservoir can include a pump that is configured to draw the sample into the reservoir through a reservoir inlet and direct the sample out of the reservoir through a reservoir outlet. The reservoir can include a diaphragm pump or other variable volume pump that can be used to result in a positive displacement of a sample, such as a syringe pump.

In other embodiments, a second outlet valve can be provided, with the second outlet valve being located downstream of the first outlet valve. When (a) is in the open position and (b), (c), and (d) are in the open position, the sanitizing fluid can flow along the fluid flow path between (a) and the second outlet valve to sanitize portions of the fluid flow path in the vicinity of (c) and (d). The second outlet valve can be a variable back-pressure regulator. In some embodiments, the second outlet valve is a thermostatically-controlled valve.

In other embodiments, when (a) and (c) are in the closed position, and (b), (d), and the second outlet valve are in the open position, gas can be introduced into the fluid flow path through (b) to purge the sanitizing fluid from at least the first and second portions of the fluid flow path. In some embodiments, the gas can function to cool the valve in a case where the sanitizing fluid is hot (e.g., steam). The sample collection valve can include a valve stem with a tapered sealing member. A portion of the valve stem can extend into the fluid flow path when the sample collection valve is in the closed position, such that sanitizing fluid introduced into the fluid flow path by the sanitizing fluid inlet valve will flow past the portion of the valve stem that extends into the fluid flow path.

In another embodiment, a method of collecting a fluid sample from an enclosed container is provided. The method can include opening a sanitizing fluid inlet valve and directing sanitizing fluid downstream through a fluid flow path past a closed sample collection valve and an open first outlet valve, and discharging the sanitizing fluid out a second outlet valve, with the second outlet valve being located downstream of the first outlet valve. A sample collection valve can be opened while the sanitizing fluid inlet valve and first outlet valve (and the gas inlet valve) are closed and a fluid sample can be drawn from the enclosed container into a variable volume reservoir along a first portion of the fluid flow path. The fluid sample can be directed out of the reservoir along a second portion of the fluid flow path and discharged out of the first outlet valve while the sanitizing fluid inlet valve and sample collection valve are closed. For a long distance embodiment, air can be pumped following the sample, allowing a relatively small volume sample to be pumped long distances.

In some embodiments, after discharging the sanitizing fluid but before drawing the fluid sample, a gas inlet valve is opened and a gas is directed downstream through the fluid flow path past the closed sample collection valve and through the first open outlet valve. The gas can be discharged through the second outlet valve to purge the sanitizing fluid from at least the first and second portions of the fluid flow path. The reservoir can include a pump that is configured to draw the sample into the reservoir through a reservoir inlet and direct the sample out of the reservoir through a reservoir outlet. In other embodiments, the pump can be a diaphragm pump, and the sanitizing fluid can include steam.

In another embodiment, a method of collecting a sample from an enclosed container is provided. The method can include directing a sanitizing fluid through a fluid flow path to sanitize or sterilize the fluid flow path. The fluid flow path can have a gas inlet port downstream of the sanitizing fluid inlet, a sample inlet port downstream of the gas inlet port, and a sample dispensing port downstream of the sample inlet port. The sanitizing fluid can be directed through the fluid flow path while the sample dispensing port is closed, and the sanitizing fluid can be exhausted through a control valve. Gas can be directed through the gas inlet port and into the fluid flow path while the sample dispensing port is closed. The gas can be exhausted through the control valve. A sample can be drawn into the fluid flow path from the enclosed container through the sample inlet port, and the sample can be dispensed out of the fluid flow path through the sample dispensing port. Additional sanitizing fluid can be directed through the fluid flow path to re-sanitize or re-sterilize the fluid flow path while the sample dispensing port is closed.

In some embodiments, drawing and dispensing the sample comprises activating a variable volume reservoir to draw at least a portion of the sample into a chamber of the variable volume reservoir and dispense the portion of the sample from the chamber of the variable volume reservoir to the sample dispensing port. In other embodiments, a back pressure can be provided by the control valve while the sanitizing fluid is directed through the fluid flow path to sanitize or sterilize the fluid flow path. The control valve can include a diaphragm valve and the back pressure can be provided by increasing air pressure on the diaphragm valve. In some embodiments, the control valve can direct sample to an end receiver/analyzer. The closure of the sample inlet port can include moving a sealing tip of a valve stem so that the sealing tip engages with the sample inlet port. When the sealing tip is engaged with the sample inlet port, at least a portion of the valve stem can extend into the fluid flow path.

In some embodiments, the sampling system is made using materials that have low heat transfer coefficients. In some embodiments, the sampling system is made using polymeric materials, such as thermoplastics and thermosetting materials. In some embodiments, the sampling system is made using composite materials. In some embodiments, the sampling system is formed by injection molding. In some embodiments, the sampling system is formed by machining and drilling.

In some embodiments, the sampling system is modular in design, allowing selection of appropriate fittings for connecting to a wide variety of apparatuses. In some embodiments, the variable volume reservoir is modular, allowing selection of a reservoir suitable for the amount of sample to be withdrawn from the enclosed container. In some embodiments the sampling system is compact to (1) reduce the hold-up volume of the sampling system, (2) allow rapid sanitizing of the sampling system, (3) allow for rapid removal of a sample from the enclosed container, or (4) any combination of (1), (2), or (3).

In some embodiments, a sample tube can dip down into the reactor from overhead allowing for the sampling into reactors above the liquid level in the container. This arrangement can be particularly helpful in a process development scale reactor.

In some embodiments, the variable volume reservoir is designed to minimize the volume of gas that remains in the sampling system after discharge from the sampling system. In some embodiments, the ratio of the sample volume collected to the hold-up volume of the sampling system is greater than 10:1, greater than 20:1, or even greater than 50:1.

In some embodiments, the variable volume reservoir is designed to push the sample collected out of the reservoir using a working fluid. In some embodiments, a positive pressure can be used via a working fluid. In other embodiments, the system can create the positive pressure without a working fluid, such as by using a syringe pump. In some embodiments, the pressure in the feed tank can be used to fill the reservoir, which is hooked to a piston—which can be pressurized (air or hydraulic fluid) to discharge the sample from the reservoir.

In some embodiments, the variable volume reservoir is designed to pull the sample from the enclosed container into the reservoir by applying a negative pressure on the variable volume reservoir. This can be particularly useful in systems with a draw tube from the top of the reactor—especially for small volume or development/experimental reactors, which may not have a port located on the bottom of the bioreactor.

The foregoing and other objects, features, and advantages of the invention will become more apparent from the following detailed description, which proceeds with reference to the accompanying figures.

DETAILED DESCRIPTION

Various embodiments of sampling systems and their methods of use are disclosed herein. The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

The terms "upstream" and "downstream" are not absolute terms; instead, those terms refer to the direction of flow of fluids within a channel or pathway. Thus, with regard to a structure through which a fluid flows, a first area is "upstream" of a second area if the fluid flows from the first area to the second area. Likewise, the second area can be considered "downstream" of the first area.

Unless otherwise indicated, all numbers expressing quantities of ingredients, properties such as molecular weight, percentages, measurements, distances, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Figure 1:
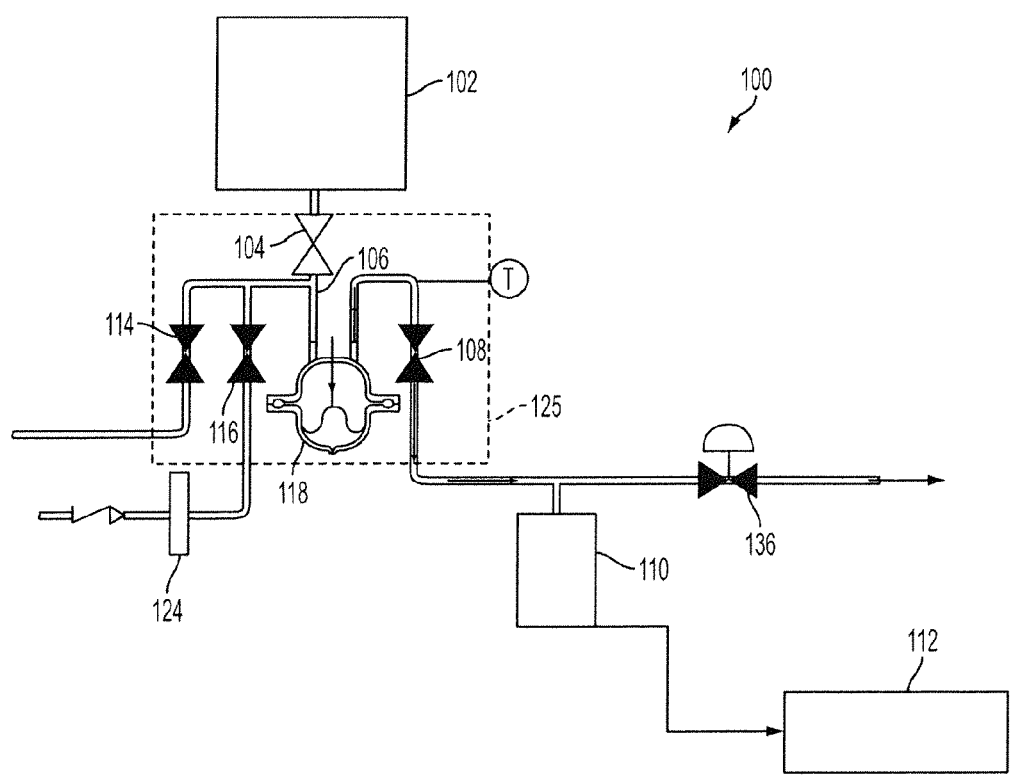
FIG. 1 illustrates a schematic view of a sampling system for obtaining samples from enclosed containers.

FIG. 1 illustrates a sampling system 100 for obtaining a sample from a bioreactor 102 or other similar containers or systems that support biologically and/or chemically active environments. Sampling system 100 includes a sample collection valve 104 that can open to allow a sample to enter a fluid flow path 106. The sample can be delivered along the flow path 106 to an outlet valve 108. Outlet valve 108 can open or close to allow or restrict, respectively, the flow of samples through outlet valve 108. After the sample exits outlet valve 108, the sample can be directed into an isolated chamber or container 110 for analysis, processing, and/or delivery to another system for analysis and/or processing. For example, the sample can be directed from chamber 110 to an automated analyzer 112, such as a bioprofile analyzer available from Nova Biomedical of Waltham, Massachusetts.

The samples that are dispensed from outlet 108 for analysis or processing are desirably representative of the materials in bioreactor 102 at the time the sample was taken. To reduce the risk of contamination, dilution, or alteration of the composition of the samples taken from sample collection valve 104 and delivered through flow path 106, a sanitizing fluid can be delivered through a portion of flow path 106 that comes into contact with the samples.

To introduce the sanitizing fluid into flow path 106, a sanitizing fluid inlet valve 114 is provided upstream of sample collection valve 104. Sanitizing fluid inlet valve 114 is operable between a closed position that restricts fluid flow through sanitizing fluid inlet valve 114 and an open position that allows fluid flow through sanitizing fluid inlet valve 114. In one embodiment, the sanitizing fluid comprises steam. In some embodiments, some or all of the valves can be biased closed.

In one embodiment, the sanitizing fluid is any fluid that can sanitize, disinfect, or sterilize the valve. The sanitizing fluid can be a liquid, a gas, or a combination thereof. Sanitizing fluids include steam, ethylene oxide, glutaraldehyde, formaldehyde, formalin, chlorine gas, hypochlorite, bromine, hypobromite, iodine, hypoiodite, bromine chloride, chlorine dioxide, ozone, hydrogen peroxide, monochloramine, dichloramine, trichloramine, quatinary ammonium salts, ethanol, 70% ethanol/water, isopropanol, 70% isopropanol/water, peroxyacetic acid, and peracetic acid. In one embodiment, the sanitizing fluid is steam. In another embodiment, the sanitizing fluid is ethylene oxide. In another embodiment, the sanitizing fluid is glutaraldehyde.

A gas inlet valve 116 can also be provided upstream of sample collection valve 104 to deliver a gas through flow path 106. The gas can eliminate and/or reduce the amount of sanitizing fluid remaining within flow path 106 after flow path 106 is exposed to the sanitizing fluid. The sanitizing fluid can clean the path and/or remove any material from previous samples in the area contacted by the sanitizing fluid. Gas inlet valve 116 is operable between a closed position that restricts the flow of gas through gas inlet valve 116 and an open position that allows the flow of gas through gas inlet valve 116. In one embodiment, the gas comprises compressed air.

To draw a sample from bioreactor 102, a variable volume reservoir 118 can be provided downstream of sample collection valve 104. Variable volume reservoir 118 can be moveable between a first position and a second position to draw a sample through sample collection valve 104 and into flow path 106. The sample can be drawn into at least a portion of variable volume reservoir 118 along a first portion of flow path 106 and discharged from variable volume reservoir 118 along a second portion of flow path 106. Variable volume reservoir 118 can comprise a diaphragm pump (as shown in FIG. 1), a syringe pump, or other similar device capable of drawing a sample from bioreactor 102.

As shown by dotted lines in FIG. 1, at least a portion of sampling system 100 can comprise a unitary structure 125. Thus, for example, unitary structure 125 can comprise sample collection valve 104, sanitizing fluid inlet valve 114, gas inlet valve 116, outlet valve 108, and at least a portion of the fluid flow path. Preferably, the entire flow path between the sanitizing fluid inlet valve 114 and the outlet valve 108 is internal to the unitary structure 125.

FIGS. 2A-2D are schematic representations of the operation of sampling system 100. As described in more detail below, sampling system 100 can be inserted into bioreactor 102 and can operate to sanitize or sterilize a flow path from the point of insertion with bioreactor 102 through the closed pathway of flow path 106. By being able to sanitize or sterilize the entire path downstream of the insertion point of sampling system 100 into bioreactor 102, the possibility of contaminating bioreactor 102 and/or the samples captured from bioreactor 102 is reduced.

Figure 2A:
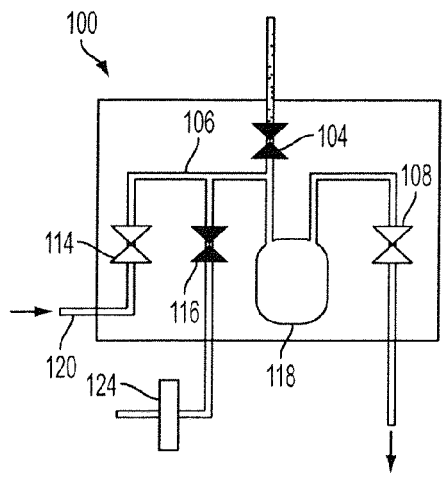
FIGS. 2A-2D illustrate schematic views of a system for obtaining samples from enclosed containers.

FIG. 2A illustrates a sanitizing procedure in which a sanitizing fluid 120 (e.g., steam) is directed into flow path 106 through an open sanitizing fluid inlet valve 114. As shown in FIG. 2A, sanitizing fluid 120 is directed along flow path 106, including along the portions of flow path 106 that are in contact with samples that are drawn from bioreactor 102 and dispensed from flow path 106. For example, sanitizing fluid 120 is directed along flow path 106 past sample collection valve 104, through variable volume reservoir 118, and out outlet valve 108. As sanitizing fluid 120 comes into contact with the internal surfaces that define flow path 106, those surfaces are sanitized or sterilized.

Figure 2B:
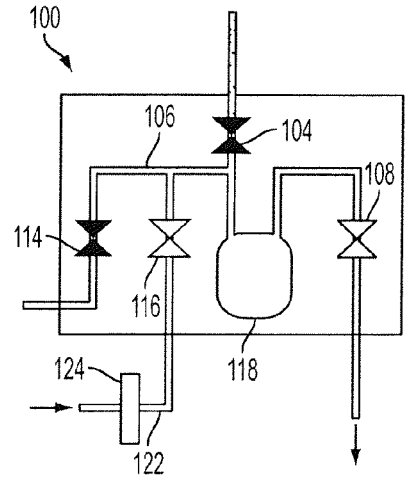

Referring now to FIG. 2B, sanitizing fluid inlet valve 114 is closed and gas inlet valve 116 is opened to allow a gas 122 (e.g., air) to enter flow path 106. As shown in FIG. 2B, gas 122 can also be directed along flow path 106, including along the portions of flow path 106 that sanitizing fluid 120 contacts. In this manner, any remaining sanitizing fluid 120 can be purged from flow path 106. If desired, a filter 124 (e.g., a sterile air filter) can be provided upstream of gas inlet valve 116 to ensure that the gas 122 that enters flow path 106 is substantially free of impurities and/or contaminants.

Figure 2C:
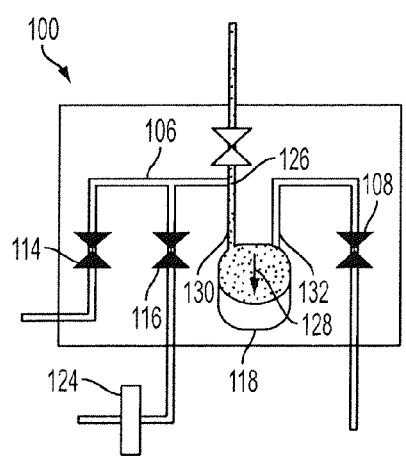
Figure 2D:
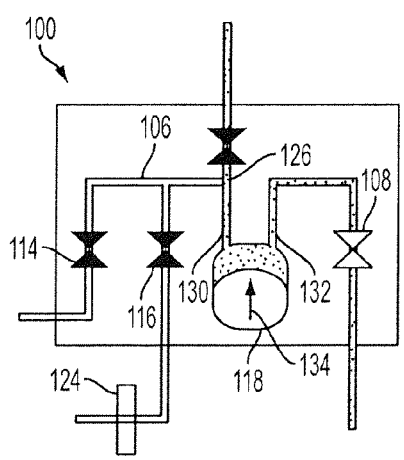

FIG. 2C illustrates the operation of variable volume reservoir 118 to draw a sample 126 from bioreactor 102 through open sample collection valve 104. As shown in FIG. 2C, variable volume reservoir 118 comprises a diaphragm pump that moves from a first volume to a second, larger volume as illustrated by arrow 128. The enlargement of the volume of variable volume reservoir 118 draws a sample through open sample collection valve 104 and into flow path 106. Variable volume reservoir 118 has an inlet 130 and an outlet 132. After sample 126 is drawn into variable volume reservoir 118, the diaphragm pump moves from the second, larger volume back to a smaller volume as illustrated by arrow 134 in FIG. 2D. The reduction of the volume of variable volume reservoir 118 discharges sample 126 through outlet 132 of variable volume reservoir 118. Sample 126 is then discharged through outlet valve 108 to be captured for analysis and/or further processing.

Referring again to FIG. 1, as sample 126 is discharged through outlet valve 108, it can be delivered to chamber 110. To facilitate delivery of sample 126 to chamber 110, a control valve 136 can be provided downstream of outlet valve 108. Control valve 136 can be configured to provide a back pressure to cause sample 126 to be directed into chamber 110 and to provide a desired back pressure along flow path 106 to facilitate the sanitizing process (e.g., FIG. 2A) and the purging process (e.g., FIG. 2B). Control valve 136 can be configured to open to allow the discharge of waste. The discharged waste can include, for example, sanitizing fluid and purging gas that has traveled along the flow path 106 to sanitize and purge excess sample materials from flow path 106.

Figure 3A:
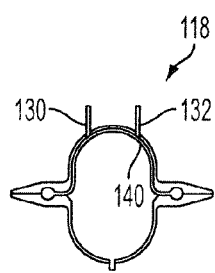
FIGS. 3A-3F illustrate a variable volume reservoir for drawing and delivery samples from enclosed containers.
Figure 3B:
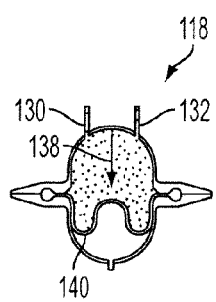
Figure 3C:
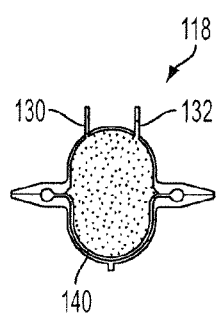
Figure 3D:
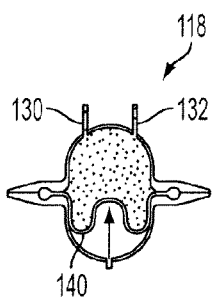
Figure 3E:
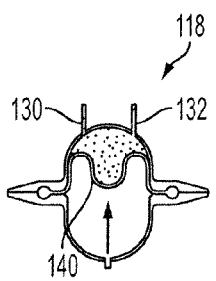
Figure 3F:
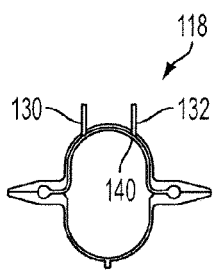

FIGS. 3A-3F illustrate an exemplary operation of a variable volume reservoir 118. FIG. 3A illustrates variable volume reservoir 118 in a first configuration with a very small volume (e.g. approximately zero volume). FIG. 3B illustrates a sample being drawn into variable volume reservoir 118 through inlet 130, thereby moving a diaphragm 140 of variable volume reservoir 118 in the direction of arrow 138. Diaphragm 140 can continue to move in the direction of arrow 138 and expand the volume of variable volume reservoir 118 until variable volume reservoir 118 reaches a second configuration with a larger volume as shown in FIG. 3C. As shown in FIGS. 3D, 3E, and 3F diaphragm 140 can then move from the second configuration to the first configuration, causing the sample contained within variable volume reservoir 118 to be discharged through outlet 132.

As shown in FIGS. 3A-3F, the variable volume reservoir 118 can comprise a housing with a first area (e.g., the lower hemispherical portion of variable volume reservoir 118 in FIGS. 3A-3F) and a second area that generally opposes the first area (e.g., the upper hemispherical portion of variable volume reservoir 118 in FIGS. 3A-3F). Diaphragm 140 can be configured to move between a first position (FIG. 3C) in which a non-sample contacting surface of diaphragm 140 lays generally flush on the first area of variable volume reservoir 118 so that the volume available for receiving a sample in variable volume reservoir is generally maximized and a second position (FIG. 3F) where the diaphragm 140 folds in on itself so that a sample contacting surface of diaphragm 140 lays generally flush on the second area of variable volume reservoir 118. In some embodiments, the surfaces of the diaphragms are not generally flush; instead, they are partially deflected, such as shown in FIG. 3B. The amount of deflection can be dependent upon the size of the sample desired.

Thus, as diaphragm 140 moves from the first position (FIG. 3C) to the second position (FIG. 3F) to dispense the sample from variable volume reservoir 118, diaphragm 140 folds in on itself to substantially expel from variable volume reservoir 118 the entire volume of the sample that was received within variable volume reservoir when diaphragm 140 was in the first position. When diaphragm 140 is in the second position, not only does diaphragm 140 substantially expel the entire volume of the sample previously contained there, but it also generally forms a barrier to entry into variable volume reservoir 118, thereby at least generally restricting entry into variable volume reservoir 118 of any fluid, including the sample that was previously contained therein.

As shown in FIGS. 3A-3F, in some embodiments, diaphragm 140 can comprise a flexible diaphragm in a housing that moves between the first and second positions as described herein. The housing can be generally spherical or it can take other shapes, such as elliptical, pyramidal, top-hat shaped, etc.

Pressure on either side of diaphragm 140 can cause operation of variable volume reservoir in the manners described herein. For example, pressure from the sample source in connection with the delivery of sample 126 from bioreactor 102 through open sample collection valve 104 (see FIG. 1) can actuate variable volume reservoir 118 to cause movement of diaphragm into the first position to receive the sample. Alternatively, if the bioreactor is under sub-atmospheric pressure, a negative pressure (i.e., vacuum) can be applied to the "back side" of the diaphragm, and then switched to a positive pressure for expelling the sample.

Similarly, the sample can be expelled from variable volume reservoir 118 by providing pressure on the non-sample contacting surface (i.e., the "back" side) of diaphragm 140. Such pressure can be provided on the back side of diaphragm 140 by delivering, for example, any fluid towards that surface as indicated, for example, by the origination of the arrow in FIGS. 3D and 3E.

Thus, in some embodiments, diaphragm 140 can comprise a flexible, inverting diaphragm that can advantageously provide a system that is capable of performing a pumping action with relatively low amounts of turbulence being introduced to the system. In addition, such a diaphragm is capable of actuation using relatively low pressures, including a relatively low sample inlet pressure to move the diaphragm from the second position (FIG. 3A, 3F) to the first position (FIG. 3C).

In some embodiments, the flexible material can have a low gas permeability to ensure the fluid used to expel the sample (e.g., air or nitrogen) doesn't permeate into the sample, thus changing the properties. EPDM can be used for the flexible material. Alternatively, other materials such as Kalrez®, Viton®, polyethylene, polyurethane, and polypropylene can also be used. The material should be able to withstand the sanitization conditions—e.g., steam.

FIGS. 4A-4D illustrate another embodiment of a sampling system 200. Sampling system 200 is generally similar to sampling system 100 and like elements are identified by similar reference numbers. The main differences between sampling system 100 and 200 are illustrated in the various figures and described in the related descriptions of those systems as included herein.

Sampling system 200 can include a sample collection valve 204, an outlet valve 208, a sanitizing fluid inlet valve 214, and a gas inlet valve 216. One or more of these valves can be configured to have a valve stem 221 and a sealing member 223. Although FIG. 4A illustrates each of these valves as having a valve stem 221 and a sealing member 223, it should be understood that the type of valve can vary. The valve stems can be actuated by springs or air, and preferably by a combination of spring- and air-actuation.

FIG. 4A illustrates a sanitizing or sterilizing process. During the process shown in FIG. 4A, sample collection valve 204, outlet valve 208, and gas inlet valve 216 are closed with sealing members 223 moved into engagement with the respective openings associated with those valves into flow path 206. Thus, for example, the sealing member 223 of sample collection valve 204 is engaged with an opening between flow path 206 and bioreactor 202 to restrict the passage of material in bioreactor 202 from entering flow path 206. At least a portion of the valve stem 221 associated with the sample collection valve 204 extends into flow path 206, but does not entirely block flow path 206. In this manner, sanitizing fluid can pass across a portion of the sample collection valve 204 (and other valves in a similar manner) to sterilize and sanitize the portions of the valve that is in flow path 206. Thus, as shown in FIG. 4A, sanitizing fluid is directed through flow path 206 across the closed gas inlet valve 216, across the closed sample collection valve 204, through the variable volume reservoir 218, across the closed outlet valve 208, and out an open control valve 236. Contaminants and other materials caught up in the sanitizing fluid can also exit control valve 236.

Figure 4B:
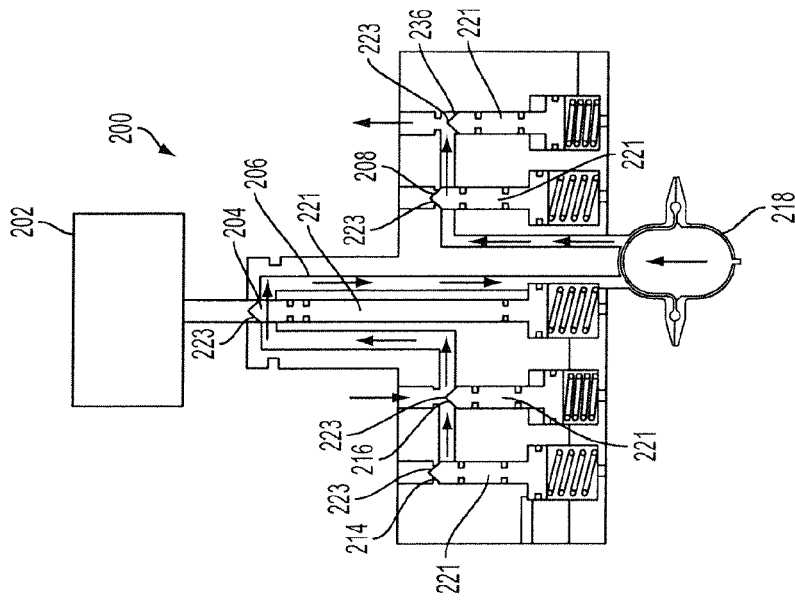
FIGS. 4A-4D illustrate schematic views of another system for obtaining samples from enclosed containers.
Figure 4A:
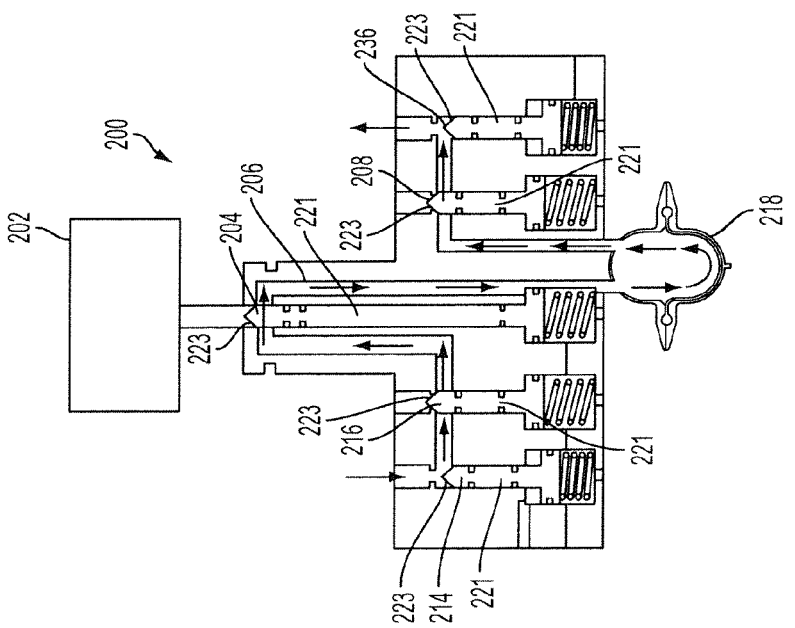

Referring to FIG. 4B, the sanitizing fluid inlet valve 214 can be closed and gas inlet valve 216 can be opened to deliver a purging gas (e.g., air) through flow path 206 to remove and/or reduce the presence of sanitizing fluid within flow path 206. The gas is directed through flow path 206 across the closed gas inlet valve 216, across the closed sample collection valve 204, through the variable volume reservoir 218, across the closed outlet valve 208, and out the open control valve 236.

Figure 4C:
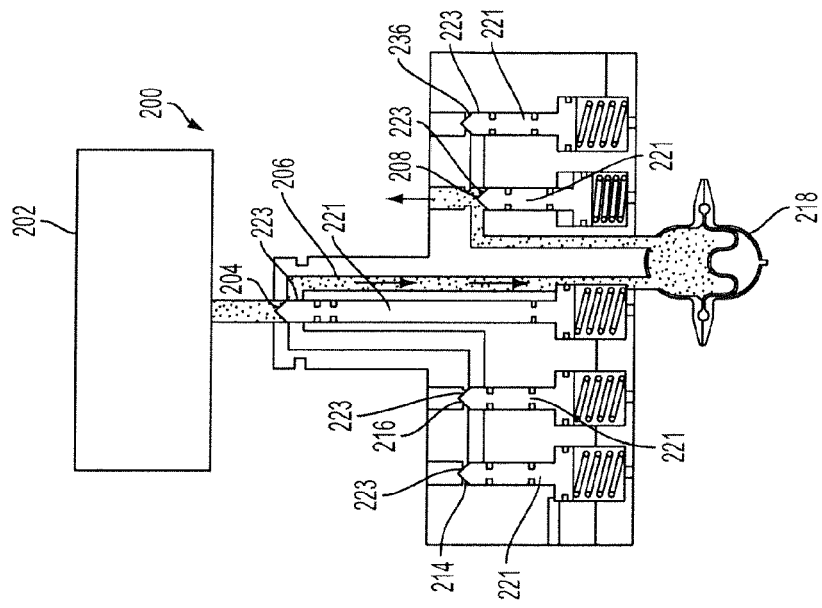
Figure 4D:
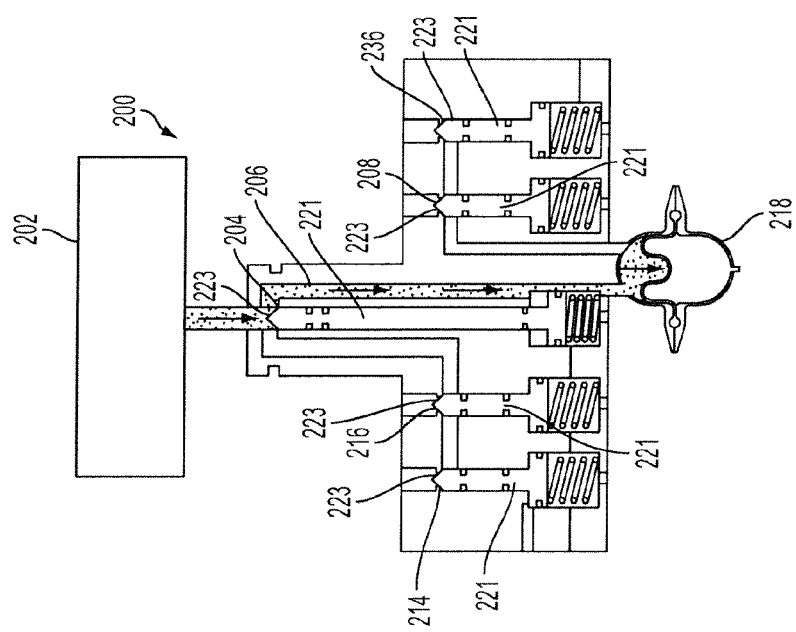

Once the gas purges the remaining sanitizing fluid from flow path 206, both the sanitizing fluid inlet valve 214 and the gas inlet valve 216 can close to allow a sample to be drawn into flow path 206. As shown in FIG. 4C, variable volume reservoir 218 draws a sample through the open sample collection valve 204 and into the volume of variable volume reservoir 218. Variable volume reservoir 218 then directs the drawn sample further downstream along flow path 206 towards outlet valve 208 as shown in FIG. 4D. Outlet valve 208 can open to allow the sample to be discharged from flow path 206.

Figure 5C:
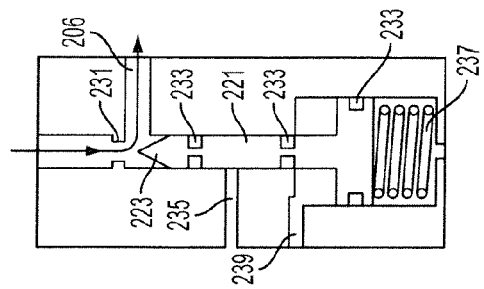
FIGS. 5A-5C illustrate enlarged views of exemplary valves that can be used with a sampling system.
Figure 5B:
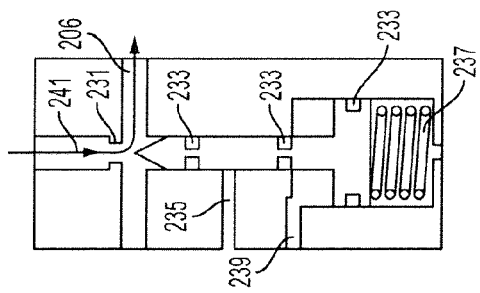
Figure 5A:
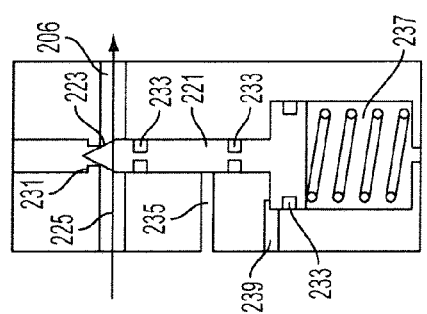

FIGS. 5A-5C illustrate enlarged views of exemplary valves that can be used with the systems disclosed in FIGS. 4A-4C. For example, FIGS. 5A and 5B illustrate a three-way bypass flow valve that can move between an open configuration (FIG. 5B) and a closed configuration (FIG. 5A). In FIG. 5A, valve stem 221 is shown extending into flow path 206 with sealing member 223 closing a port 231 (e.g., a gas inlet port, a sample collection inlet port, a sample collection outlet port) into flow path 206. In the closed configuration, fluid can flow past valve stem 221 as shown by arrow 225. One or more sealing rings 233 (e.g., O-rings) can at least partially surround valve stem 221 to restrict the flow of fluid out of flow path 206 in the area of valve stem 221. In addition, a weep hole 235 can be provided to further remove any moisture of other fluids that may move past sealing rings 233.

A spring 237 can be provided to bias valve stem 221 towards the closed configuration (FIG. 5A) and to ensure that sealing member 223 seats itself properly with port 231. An air inlet 239 can be provided adjacent valve stem 221 to move valve stem 221 from the closed configuration (FIG. 5A) to the open configuration (FIG. 5B). Compressed air or other fluids can be directed through air inlet 239, causing valve stem 221 to move downward as shown in FIG. 5B. As valve stem 221 moves downward, sealing member 223 moves out of engagement with port 231, allowing fluid to pass through port 231 and enter flow path 206 as shown by arrow 241.

FIG. 5C illustrates a two-way valve that is moveable between a closed configuration (not shown) and an open configuration (FIG. 5C). As shown in FIG. 5C, a valve stem 221 with a sealing member 223 can move into an open configuration in the same manner as that shown in FIG. 5B. Such a valve can be used, for example, with a port 231 that is configured to be opened and closed to allow fluid to flow into the pathway, such as a sanitizing fluid inlet port or a waste outlet port.

Figure 6:
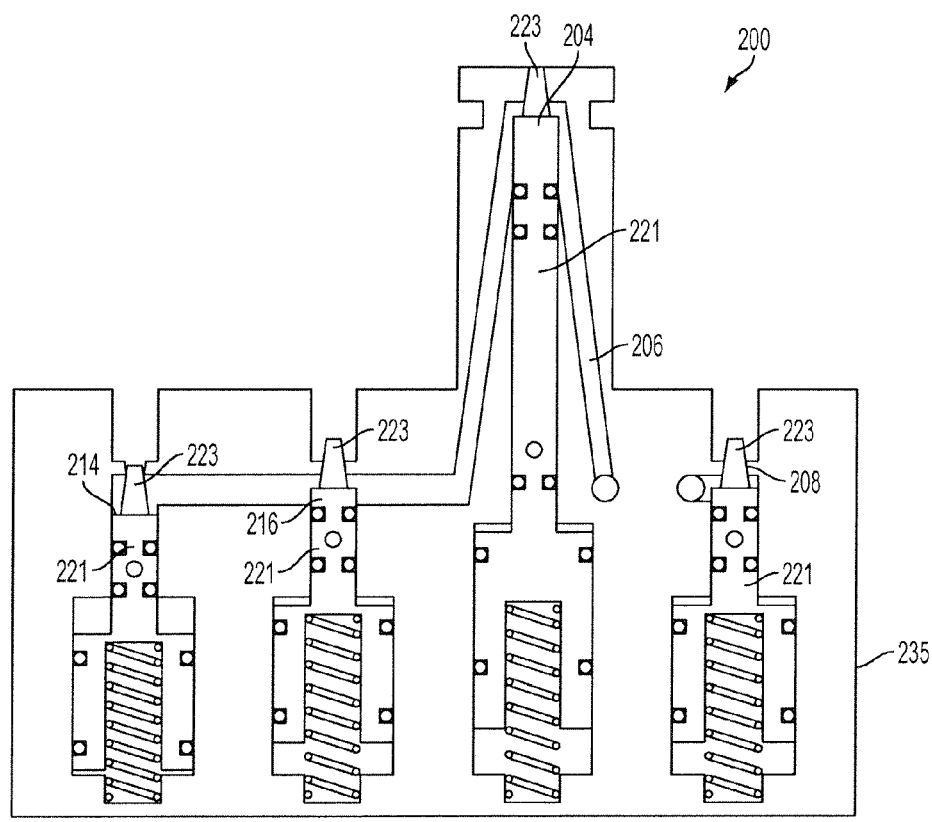
FIG. 6 illustrates a cross-sectional view of a system for obtaining samples from enclosed containers.

FIG. 6 illustrates a cross-sectional view of a portion of another exemplary sampling system 200, shown with an angled fluid path 206 between the sanitizing fluid inlet valve 214 and the outlet valve 208. Sample collection valve 204 extends from a main body 235 of sampling system 200 to facilitate coupling of sample collection valve 204 with bioreactor 202 (not shown in FIG. 6).

Figure 7:
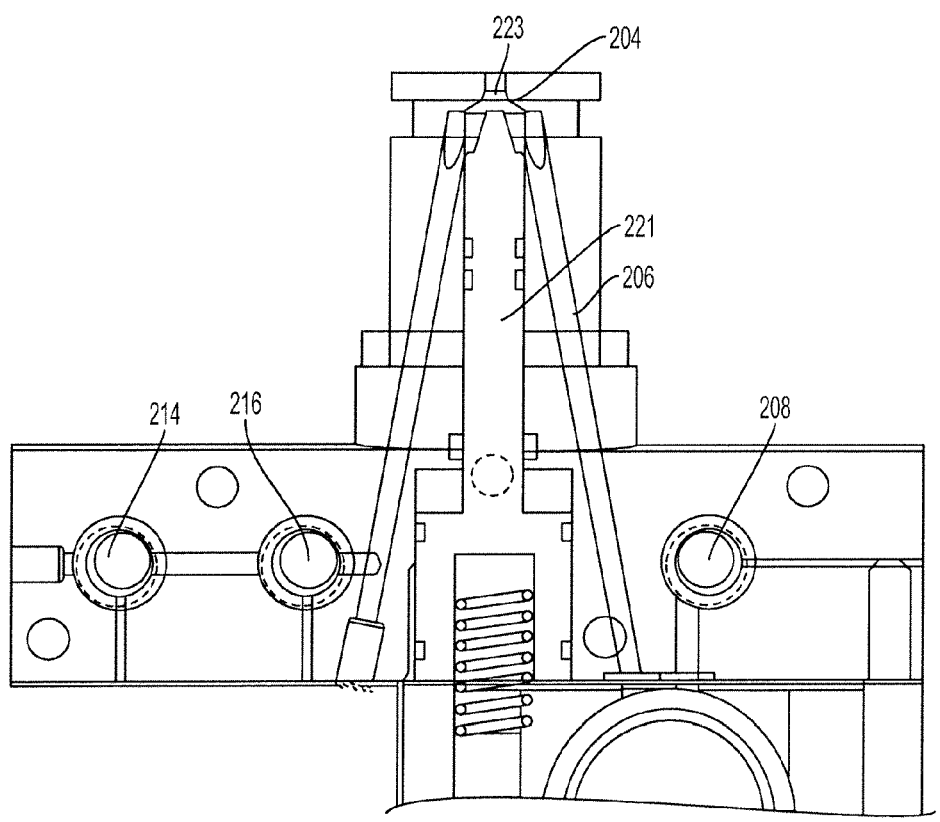
FIG. 7 illustrates a partial cross-sectional view of a system for obtaining samples from enclosed containers.
Figure 8:
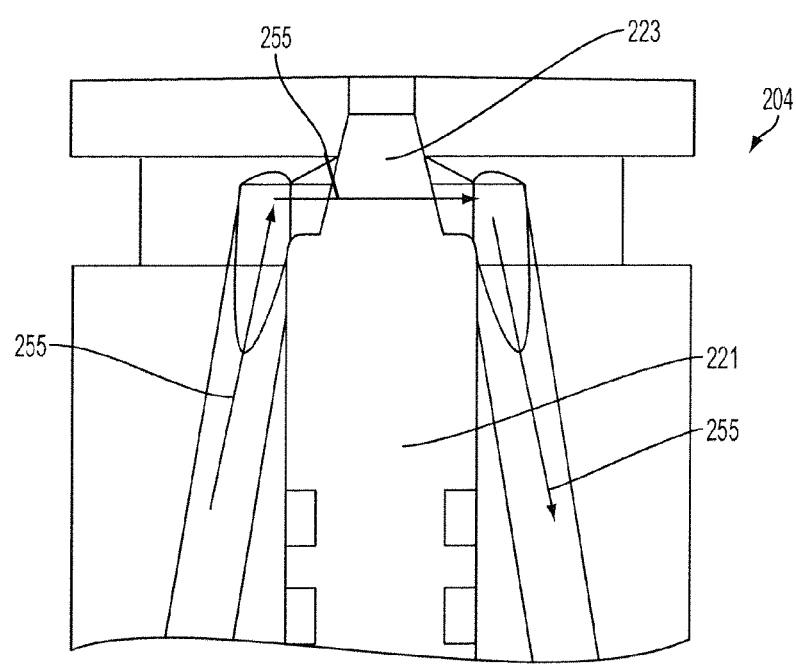
FIG. 8 is an enlarged view of a portion of the system shown in FIG. 6.

FIGS. 7 and 8 illustrate views of portions of another exemplary sampling system 200, also having an angled fluid path 206 between the sanitizing fluid inlet valve 214 and the outlet valve 208. As shown in the enlarged partial cross-sectional view of FIG. 8, when sample collection valve 204 is in a closed position (e.g., with a sealing member 223 extending into an opening between the bioreactor and flow path 206), sanitizing fluid can flow around the end of valve stem 221. Thus, for example, as shown by arrows 255, sanitizing fluid can pass around a portion of sample collection valve 204, thereby improving sanitization or sterilization of the area adjacent the opening extending into the bioreactor.

Moreover, by forming sample collection valve with a sealing member 223 that tapers from valve stem 221, the area of contact between sealing member 223 and the opening can be reduced. To provide improved sealing characteristics, in some embodiments, the tip of the valve stem can extend at an angle of greater than 50 degrees from the body of the valve stem and, more preferably at an angle of greater than 70 degrees and, even more preferably at an angle of about 80 degrees.

In some embodiments, sealing member 223 (FIG. 8) can be formed of a polymeric material that is softer than the material of the seat, into which sealing member 223 extends. In some embodiments, the seat can be formed of a more rigid polymer material. For example, the seat can be made of most teflons (PTFE, PFA, ETFE, etc.) and the seat can be made of a high performance, high temperature, harder thermoplastic. (PEEK, PEI, PPSU, PSU, etc.). For the stem, creep resistant PFA is preferred and PEEK is preferred for the rest of the body. PEEK and teflons are preferable materials due to their relatively chemically inert behavior.

In this manner, sealing member 223 can extrude into the seat to form a tighter seal. In addition, as shown in FIG. 7, sealing member 223 can have a steeper cone shape than the hollow cone seat, thereby allowing sealing member 223 to extrude into the seat to form a positive seal. The design allows for a variable sealing area, causing the stem to deform until the stress on the materials at the seal is within the elastic modulus of the valve stem, allowing a good seal even with relatively wide tolerances on the angles of the seat and stem. This configuration can have several advantages. For example, because the seat can be formed as a cone-shaped hole as shown in FIG. 7, the opening can be very small, allowing it to be easily incorporated into a small conduit and amenable to sterilization in the manners described herein (e.g., by steam). Moreover, when one or both of the sealing member and seat are formed of polymers, the heat up and cool down times associated with those parts can be faster than the times associated with other materials, such as steel or other metals.

In some embodiments, the sealing member and valve stem can be formed of the same polymeric material, which can further improve operation by reducing complexities of manufacturing and permitting the sealing member and valve stem component to be more compact.

Figure 9:
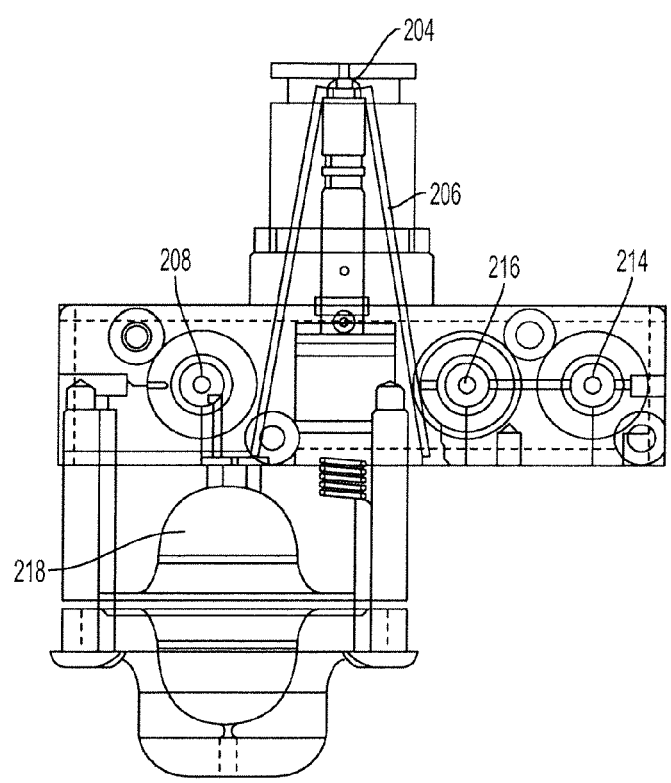
FIG. 9 illustrates another embodiment of a system for obtaining samples from enclosed containers.

FIG. 9 illustrates another embodiment of sampling system 200, with a variable volume reservoir 218 integrally formed with the sampling system structure. Variable volume 218 comprises a diaphragm pump connected flow path 206 to draw samples from the bioreactor (not shown) to which sampling system 200 is coupled.

As described above with respect to FIG. 1, a control valve 136 can be provided downstream of outlet valve 108. Control valve 136 can be configured to provide a desired back pressure along flow path 106 to facilitate the sanitizing process (e.g., FIG. 2A), the purging process (e.g., FIG. 2B), and/or the sample collection process (e.g., FIG. 2D). For example, during the sanitizing process, it is desirable to keep the sanitizing fluid at a desired temperature for a desired length of time (e.g., if steam is the sanitizing fluid it can be desirable to maintain the steam at about 121° C.). By providing back pressure via the control valve, the control valve can help direct the sample and the temperature within the flow path during the sanitizing process can be more easily maintained.

Figure 10:
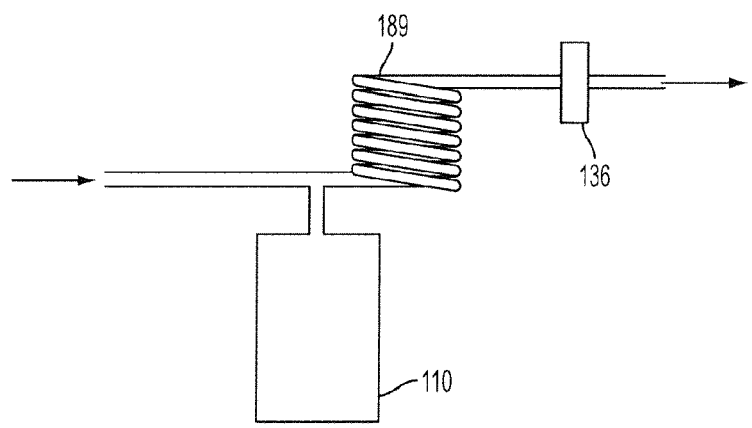
FIG. 10 illustrates a partial view of a portion of a system for obtaining samples from enclosed containers.
Figure 12:
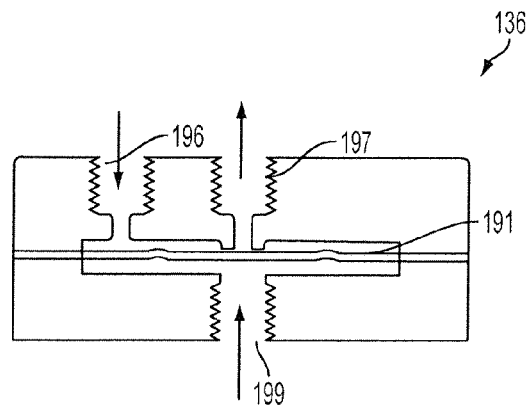
FIG. 12 illustrates another view of the control valve of FIG. 10.
Figure 11:
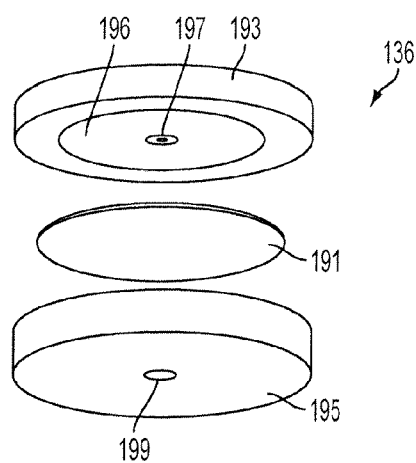
FIG. 11 illustrates a control valve for use with a system for obtaining samples from enclosed containers.
Figure 13A:
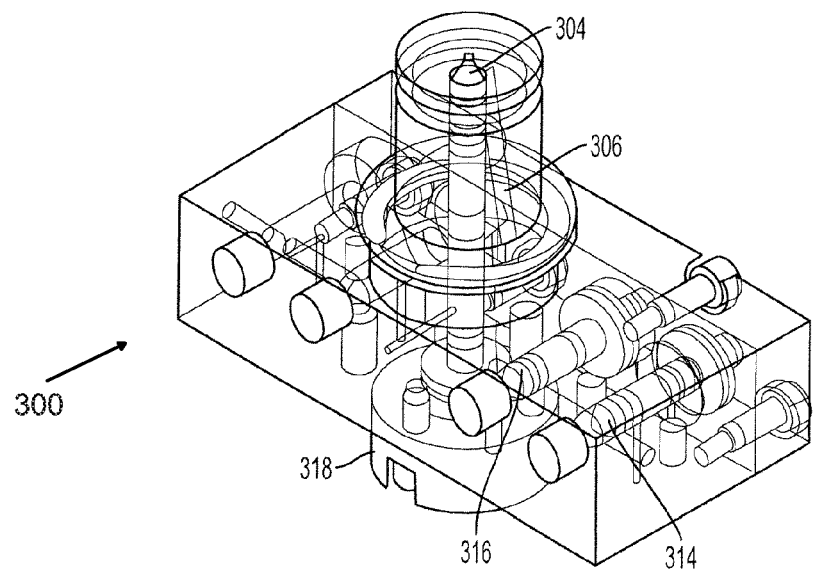
FIGS. 13A-13D illustrate various views of another embodiment of a system for obtaining samples from enclosed containers.
Figure 13B:
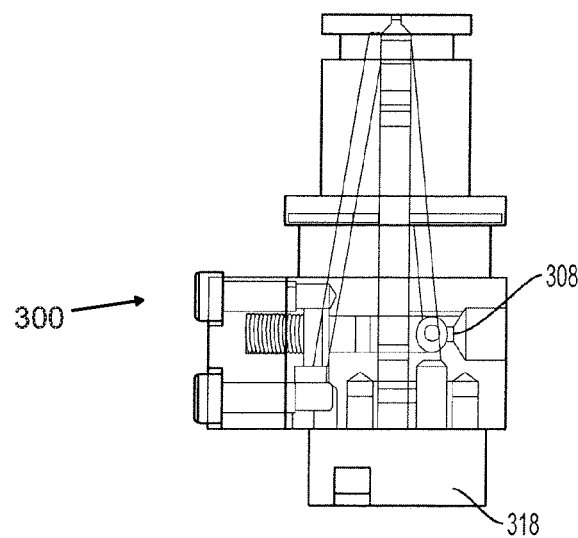
Figure 13C:
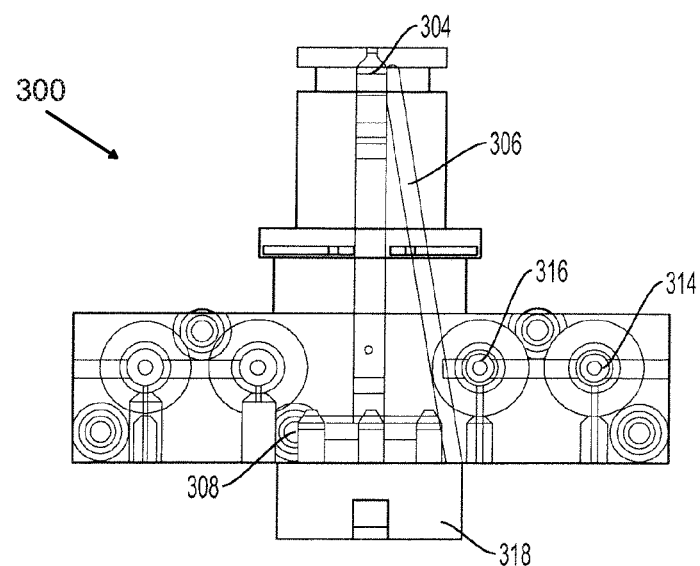
Figure 13D:
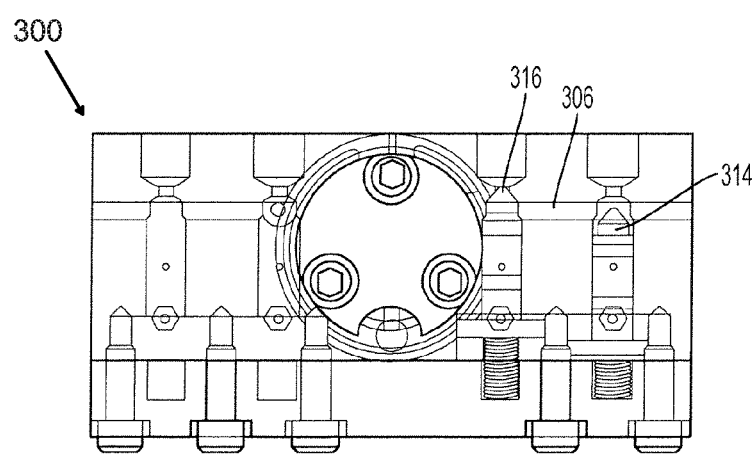

FIGS. 10-12 illustrate an embodiment of a control valve 136 that comprises a diaphragm valve. As shown in FIGS. 11 and 12, control valve 136 can comprise a diaphragm 191 positioned between two wall members 193, 195 to restrict and/or allow flow through the control valve. For example, first wall member 193 can comprise an inlet 196 and an outlet 197. Movement of diaphragm 191 towards first wall member 193 restricts passage of fluid through inlet 196 and outlet 197. To provide for movement of diaphragm 191, a control air inlet 199 can be provided on the opposing second wall member 195. An increase in air pressure at control air inlet 199 causes diaphragm 191 to move towards first wall member 193, while a decrease in air pressure at control air inlet 199 causes diaphragm 191 to move away from first wall member 193. In this manner, back pressure can be adjusted adjacent the outlet valve of the sampling system as needed or desired.

Referring again to FIG. 10, a holding coil 189 can be provided to contain a sample during a sample collection processing. Holding coil 189 can provide a volume into which a sample can be drawn. In operation, the sample is pumped or drawn into holding coil 189 and then drawn into the chamber from holding coil 189. This can allow larger samples to be drawn and, if the sample drawn is larger than the sample delivered into chamber 110, ensure that the sample delivered into chamber 110 is from a central region of the drawn sample. By capturing a central portion of the sample, the likelihood of that sample being contaminated within the flow path of the sampling system can be further reduced.

FIGS. 13A-13D illustrate various views of an integral sampling system 300. As in other embodiments, sampling system 300 includes a sample collection valve 304, an outlet valve 308, a sanitizing fluid inlet valve 314, a gas inlet valve 316, and a flow path 306 extending along these valves. A variable volume reservoir 318 can comprise a diaphragm pump that is configured to draw fluid from a bioreactor through an open sample collection valve 304. Sampling system 300 can be formed of an integral structure that can be coupled to a bioreactor to drawn samples therefrom.

Figure 14:
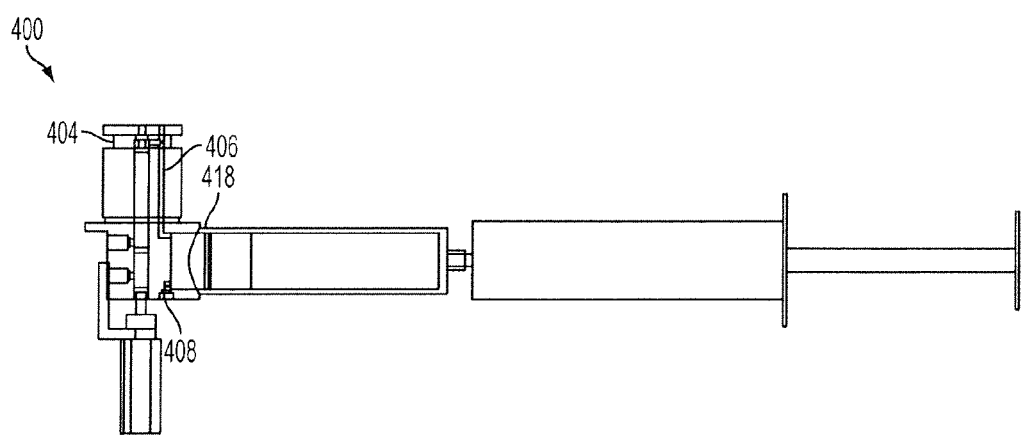
FIG. 14 illustrates a variable volume reservoir that comprises a syringe-type device.
Figure 15:
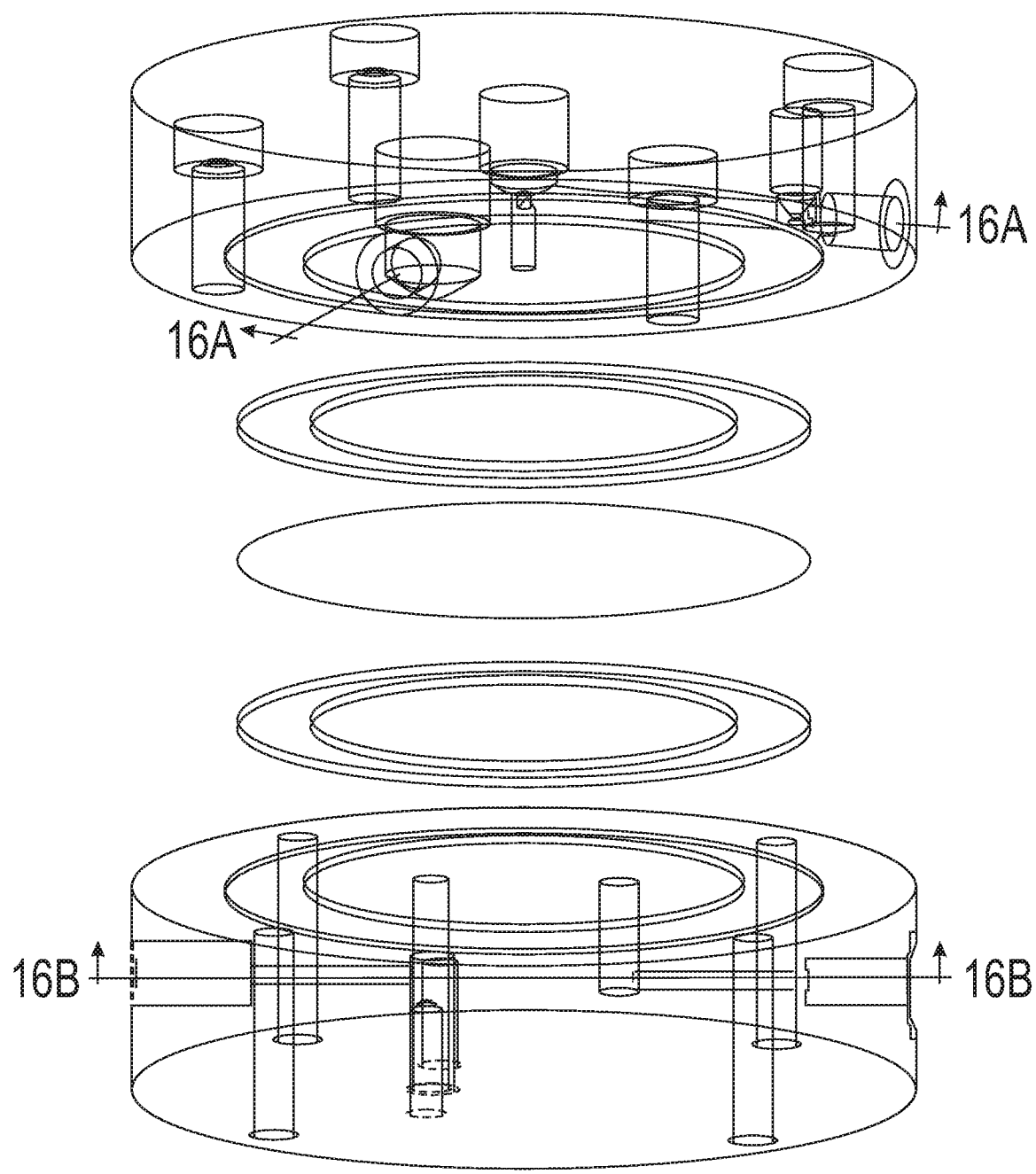
FIG. 15 illustrates another control valve for use with a system for obtaining samples from enclosed containers.
Figure 16:
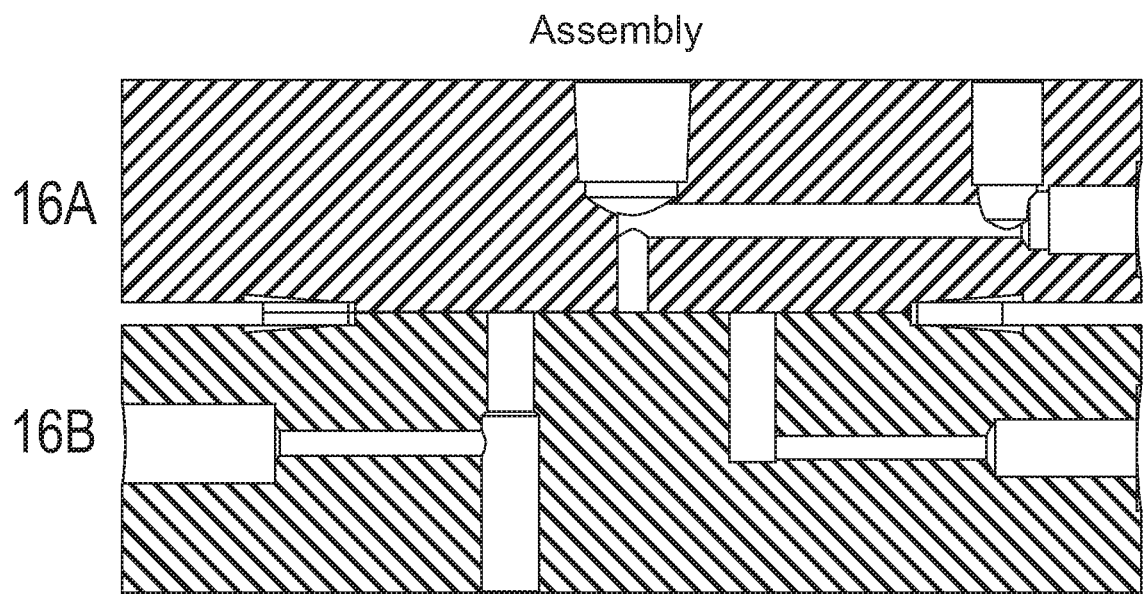
FIG. 16 illustrates a cross-sectional view of the valve shown in FIG. 15.
Figure 17:
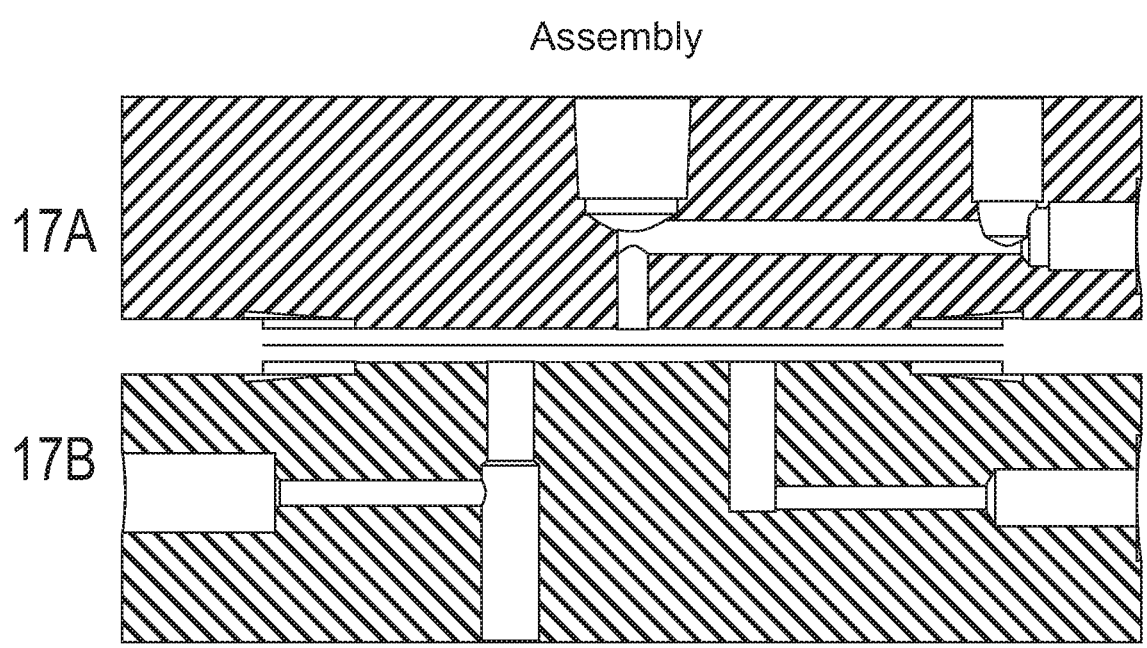
FIG. 17 illustrates a cross-sectional view of the valve shown in FIG. 15.
Figure 18:
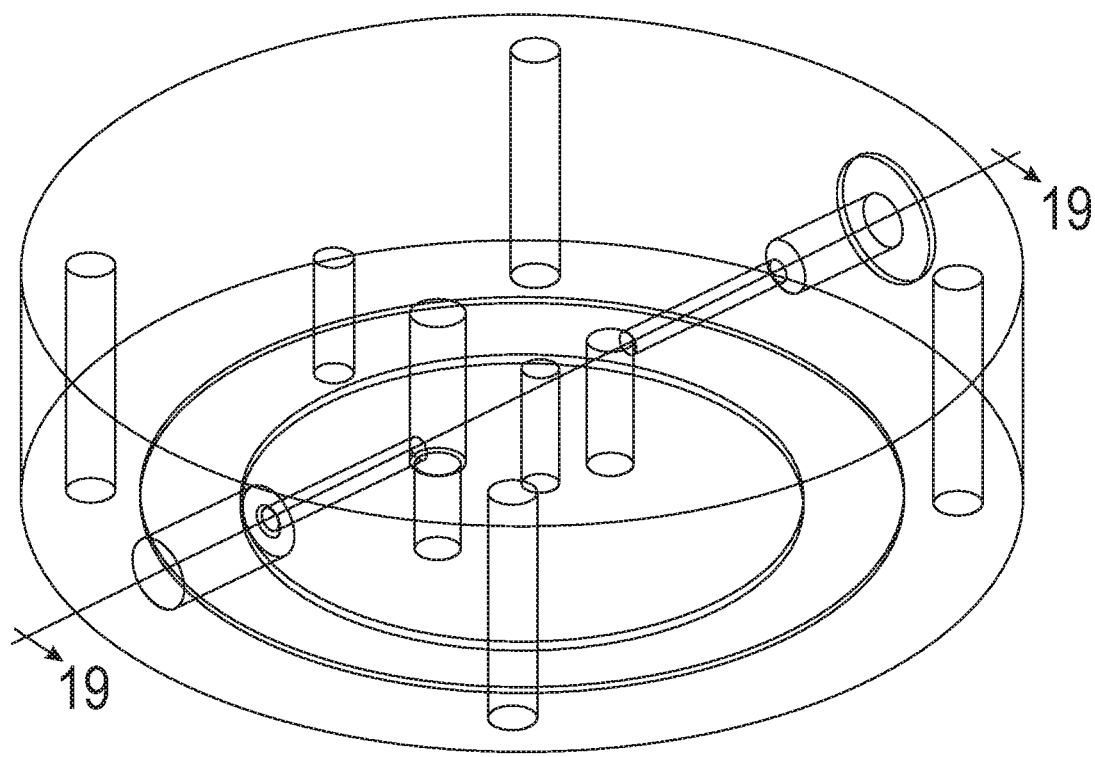
FIG. 18 illustrates the control valve of FIG. 15 shown from a liquid side.
Figure 19:
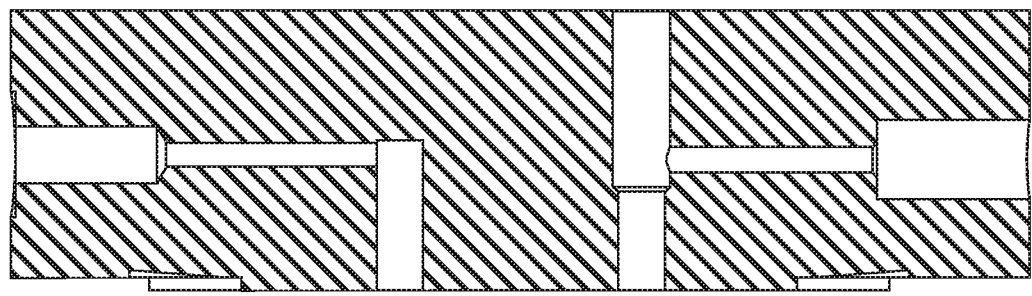
FIG. 19 illustrates a cross-sectional view of the valve of FIG. 15.
Figure 20:
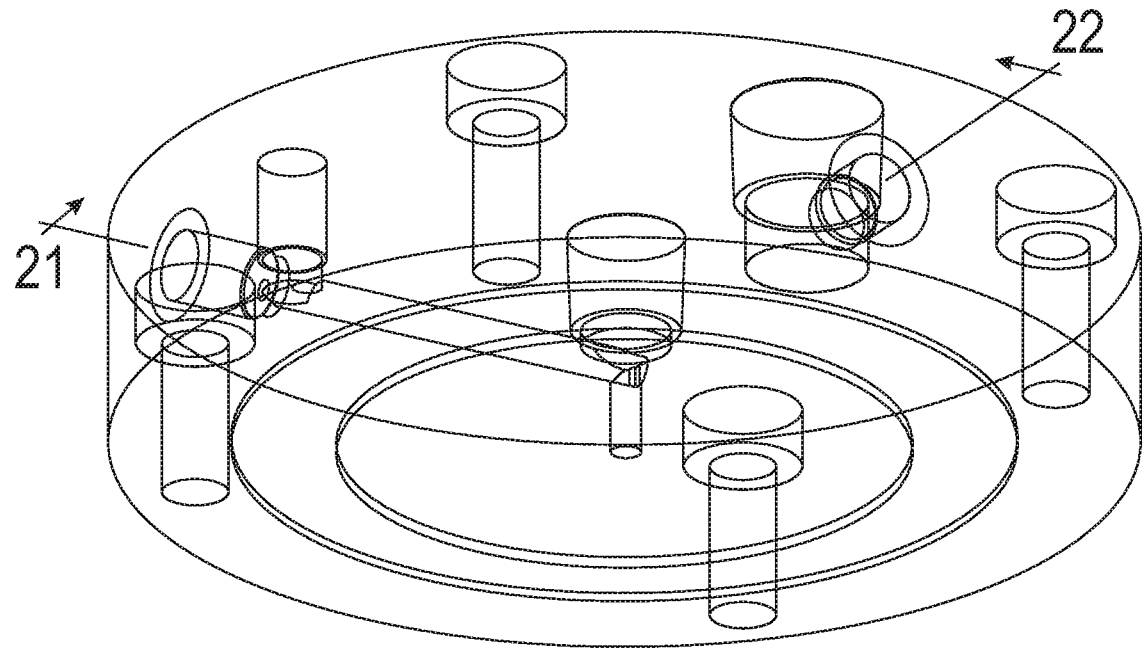
FIG. 20 illustrates the control valve of FIG. 15 shown from an air side.
Figure 21:
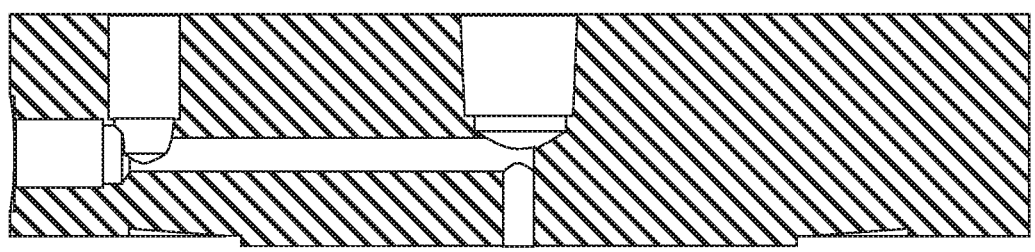
FIG. 21 illustrates a cross-sectional view of the valve of FIG. 15.
Figure 22:
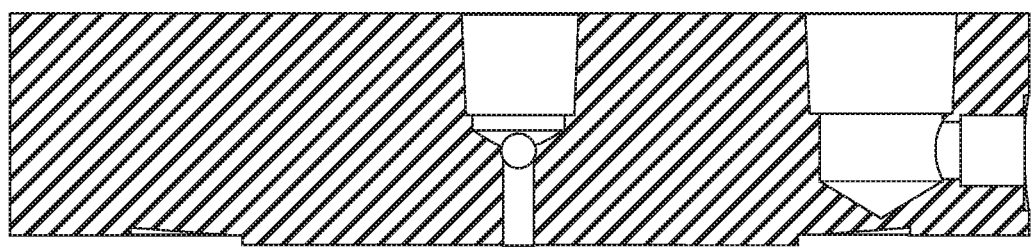
FIG. 22 illustrates a cross-sectional view of the valve of FIG. 15.

As discussed above, the variable volume reservoirs can include a diaphragm pump or other similar structures. FIG. 14 illustrates a sampling apparatus 400 that comprises a variable volume reservoir 418. Sampling apparatus 400 can generally function similar to other sampling apparatuses described herein. However, instead of the diaphragm pumps illustrated in the other embodiments, variable volume reservoir 418 is a syringe-type pump. Thus, by operating the syringe-type pump to increase a volume in variable volume reservoir 418, the sample is drawn through open sample collection valve 404, into flow path 406, and into the reservoir of the syringe-type pump. As the volume in the syringe-type pump is decreased, the sample is discharged from the reservoir of the variable volume reservoir 418 and out the outlet valve 408.

EXAMPLE

Comparison of Sampling System Valve to Conventional Manual Sampling

An automated aseptic sampling (AAS) system similar to that described above with respect to FIG. 1 was installed on a bioreactor to draw samples and deliver them to an analyzer without contamination and gas exchange, while maintaining sterility of the bioreactor. Automatic samples taken using the AAS system were compared to conventional manual sampling techniques. Manual samples were taken from the chamber and introduced to a Nova® Biomedical Bioprofile® FLEX autosampler (Waltham, MA) using a syringe. The samples were then analyzed to compare results.

For the first comparison test, the AAS system was attached to a 30 L New Brunswick bioreactor (Edison, NJ) containing NS0 culture grown in media. As the AAS was drawing sample through an independent port, manual samples were drawn to provide a sample pair. AAS and manual samples were both introduced to the FLEX autosampler for analysis of pH and carbon dioxide (measuring cell activity). Sample error was defined as the difference between the AAS system and manual sampling for a single sample pair. Errors from the sample pairs were averaged to determine variability. The results are shown in Tables 1 and 2 and demonstrate that the AAS is as accurate as manual sampling.

TABLE 1

Analysis of pH Results

| Sample ID | pH AAS | pH Manual | pH Difference |
|---|---|---|---|
| 1 | 7.196 | 7.196 | 0 |
| 2 | 7.183 | 7.175 | 0.008 |
| 3 | 7.198 | 7.181 | 0.017 |
| 4 | 7.177 | 7.163 | 0.014 |
| 5 | 7.182 | 7.166 | 0.016 |
| Average Difference | | | 0.011 |

TABLE 2

Analysis of Carbon Dioxide Results

| Sample ID | $pCO_2$ (mmHg) AAS | $pCO_2$ (mmHg) Manual | $pCO_2$ Error (%) |
|---|---|---|---|
| 1 | 58.3 | 56.9 | 2.5% |
| 2 | 60.9 | 61.3 | 0.7% |
| 3 | 57.1 | 57.3 | 0.3% |
| 4 | 59.1 | 61.1 | 3.3% |
| 5 | 57.6 | 60.9 | 5.4% |
| Average Difference | | | 2.4% |

For the second comparison test, an aliquot of cells was added to a stainless steel cylindrical vessel. The vessel was inverted several times to mix. Automatic samples were taken by the AAS system attached to the bottom of the vessel. Manual samples were removed via pipette through the top of the vessel. Automatic and manual samples were introduced to the FLEX autosampler, and sample pairs were analyzed for comparison. Results in Table 3 demonstrate accurate sampling using the AAS valve of the invention.

TABLE 3

Cell Count Testing Results

| Sample ID | Total Density (cells/mL) AAS | Total Density (cells/mL) Manual | Total Density Error | Viable Density (cells/mL) AAS | Viable Density (cells/mL) Manual | Viable Density Error | Viability (%) AAS | Viability (%) Manual | Viability Error |
|---|---|---|---|---|---|---|---|---|---|
| 1 | 61.31 | 70.26 | -12.7% | 57.69 | 65.75 | -12.3% | 94.1 | 93.6 | 0.5% |
| 2 | 31.43 | 33.15 | -5.2% | 29.58 | 31.07 | -4.8% | 94.1 | 93.7 | 0.4% |
| 3 | 125.38 | 135.66 | -7.6% | 119.89 | 128.86 | -7.0% | 95.6 | 95 | 0.6% |
| 4 | 136.08 | 133.63 | 1.8% | 124.73 | 123.13 | 1.3% | 91.7 | 92.1 | -0.4% |
| 5 | 125.35 | 141.11 | -11.2% | 116.34 | 130.05 | -10.5% | 92.8 | 92.2 | 0.7% |
| 6 | 71.15 | 72.52 | -1.9% | 64.6 | 66.17 | -2.4% | 90.8 | 91.2 | -0.4% |
| 7 | 36.14 | 36.93 | -2.1% | 32.23 | 33.32 | -3.3% | 89.2 | 90.2 | -1.1% |
| 8 | 126.45 | 141.59 | -10.7% | 116.61 | 130.89 | -10.9% | 92.2 | 92.4 | -0.2% |
| 9 | 135.59 | 137.99 | -1.7% | 126.65 | 127.56 | -0.7% | 93.4 | 92.4 | 1.1% |
| 10 | 147.26 | 135.35 | 8.8% | 136.28 | 125.44 | 8.6% | 92.5 | 92.7 | -0.2% |
| 11 | 80.75 | 72.54 | 11.3% | 69.36 | 66.31 | 4.6% | 85.9 | 91.4 | -6.0% |
| 12 | 153.91 | 135.63 | 13.5% | 133.44 | 124.65 | 7.1% | 86.7 | 91.9 | -5.7% |
| 13 | 137.91 | 137.47 | 0.3% | 127.28 | 125.68 | 1.3% | 92.3 | 91.4 | 1.0% |
| 14 | 62.96 | 72.34 | -13.0% | 57.38 | 64.81 | -11.5% | 91.1 | 89.6 | 1.7% |
| 15 | 38.68 | 40.28 | -4.0% | 34.54 | 35.06 | -1.5% | 89.3 | 87 | 2.6% |
| 16 | 139.07 | 143.25 | -2.9% | 128.15 | 130.79 | -2.0% | 92.1 | 91.3 | 0.9% |
| 17 | 74.44 | 73.56 | 1.2% | 67.49 | 66.72 | 1.2% | 90.7 | 90.7 | 0.0% |
| 18 | 32.98 | 36.93 | -10.7% | 30.21 | 32.91 | -8.2% | 91.6 | 89.1 | 2.8% |
| 19 | 147.19 | 136.29 | 8.0% | 138.86 | 126.41 | 9.8% | 94.3 | 92.7 | 1.7% |
| 20 | 131.98 | 135.08 | -2.3% | 122.34 | 124.3 | -1.6% | 92.7 | 92 | 0.8% |
| Average Error | | | 6.5% | | | 5.5% | | | 1.4% |

*Note:
NS0 cells grown in fed-batch culture were removed from bioreactor just prior to addition into sampling vessel.

The prototype AAS system of the invention was further tested to demonstrate long-term operation and removal of representative bioreactor samples without bioreactor contamination. The AAS system was mounted on a 30-L bioreactor and tested, using the test schematic noted above, which is similar to that shown in FIG. 1. The AAS valve was cycled every 30 minutes for 3 weeks, for a total of more than 1200 cycles. Cycles consisted of heating the valve to more than 121° C. (measured at the outlet) for 20 minutes and then cooling it to about 50° C. before dispensing a 20-mL sample. Five days before the end of the test, the valve was intentionally contaminated five times with $E.\ coli$ (once on one day and twice a day for two days) with no resulting contamination of the bioreactor. These tests demonstrate successful operation of the AAS system.

Additional tests of the AAS/Flex autosampler were performed at the 30-L scale. At a scheduled time point, the AAS system transferred a sample from the bioreactor to the FLEX and commanded the FLEX to take the delivered sample and analyze it. It then cleaned and sanitized itself in preparation for the next sample. A manual sample was taken within about 15 minutes of the automated sample. Cell density and viability measurements from the AAS/Flex autosampler were compared to measurements from manual sampling, to demonstrate that the AAS/Flex autosampler results are in agreement with results obtained from manual samples. Comparison of results in Table 4 shows accurate sampling using the AAS valve of the invention.

TABLE 4

Cell Count Performance of the AAS/Flex Autosampler @ 30 L Scale

| Day | Viable Cell Density (1E6 cells/mL) | | % Difference | Viability (%) | | % Difference |
|---|---|---|---|---|---|---|
| | AAS | Manual | | AAS | Manual | |
| 0.00 | 0.70 | n/a | n/a | 96.90 | n/a | n/a |
| 0.37 | 0.87 | 0.80 | 8.06 | 98.70 | 98.90 | 0.20 |
| 0.82 | 1.02 | 0.88 | 13.78 | 99.00 | 99.00 | 0.00 |
| 1.84 | 2.05 | 1.67 | 18.60 | 99.40 | 99.20 | 0.20 |
| 3.06 | 3.55 | 3.54 | 0.28 | 98.10 | 98.40 | 0.30 |
| 3.40 | 4.58 | 4.38 | 4.47 | 98.40 | 98.20 | 0.20 |
| 3.83 | 5.19 | 4.55 | 12.39 | 98.80 | 98.80 | 0.00 |
| 4.10 | 5.94 | 5.93 | 0.29 | 98.70 | 98.70 | 0.00 |
| 4.41 | 6.65 | 6.20 | 6.79 | 98.90 | 98.90 | 0.00 |
| 4.80 | 7.15 | 7.51 | 5.14 | 99.30 | 99.10 | 0.20 |
| 5.42 | 9.18 | 8.64 | 5.91 | 99.10 | 98.80 | 0.30 |
| 5.80 | 10.05 | 9.93 | 1.13 | 99.30 | 99.10 | 0.20 |
| 6.08 | 11.70 | 11.32 | 3.26 | 99.20 | 99.20 | 0.00 |
| 6.39 | 11.78 | 11.20 | 4.92 | 99.20 | 99.20 | 0.00 |
| 6.80 | 12.39 | 12.13 | 2.10 | 98.80 | 98.90 | 0.10 |
| 7.10 | 13.13 | 13.71 | 4.42 | 98.30 | 98.20 | 0.10 |
| 7.38 | 14.30 | 12.34 | 13.72 | 98.00 | 98.10 | 0.10 |
| 7.86 | 14.59 | 14.63 | 0.29 | 98.20 | 98.00 | 0.20 |
| 8.93 | 15.06 | 14.72 | 2.27 | 96.80 | 96.60 | 0.20 |
| 9.78 | 14.93 | 15.10 | 1.11 | 95.20 | 95.30 | 0.10 |
| 10.11 | 14.86 | 15.28 | 2.79 | 94.90 | 94.10 | 0.80 |
| 10.40 | 14.69 | 15.40 | 4.83 | 94.70 | 93.90 | 0.80 |
| 11.91 | 14.05 | 14.24 | 1.30 | 92.70 | 93.00 | 0.30 |
| 12.70 | 13.16 | 12.84 | 2.44 | 91.00 | 91.50 | 0.50 |
| 13.77 | 12.05 | 12.21 | 1.29 | 87.40 | 89.50 | 2.10 |
| Average % Difference | | | 5.07% | | | 0.29% |

Results in Table 5 show pH measurements of samples taken using the AAS/Flex autosampler compared to measurements from manual sampling. Table 5 further demonstrates accurate sampling using the AAS valve of the invention.

TABLE 5 pH Performance of the AAS/Flex Autosampler @ 30 L Scale

| | pH | | |
|---|---|---|---|
| Day | AAS | Manual | Difference |
| 0.37 | 7.232 | 7.221 | 0.011 |
| 0.82 | 7.221 | 7.241 | 0.02 |
| 1.84 | 7.171 | 7.227 | 0.056 |
| 3.06 | 6.93 | 6.943 | 0.013 |
| 3.4 | 6.936 | 6.952 | 0.016 |
| 3.83 | 6.927 | 6.95 | 0.023 |
| 4.1 | 6.922 | 6.943 | 0.021 |
| 4.41 | 6.927 | 6.945 | 0.018 |
| 4.8 | 6.918 | 6.929 | 0.011 |
| 5.42 | 6.917 | 6.951 | 0.034 |
| 5.8 | 6.906 | 6.924 | 0.018 |
| 6.08 | 6.894 | 6.942 | 0.048 |
| 6.39 | 6.903 | 6.943 | 0.04 |
| 6.8 | 6.915 | 6.932 | 0.017 |
| 7.1 | 6.912 | 6.955 | 0.043 |
| 7.38 | 6.938 | 6.995 | 0.057 |
| 7.86 | 6.971 | 7.003 | 0.032 |
| 8.93 | 7.01 | 7.056 | 0.046 |
| 9.78 | 7.018 | 7.066 | 0.048 |
| 10.11 | 7.035 | 7.088 | 0.053 |
| 10.40 | 7.042 | 7.102 | 0.06 |
| 11.91 | 7.116 | 7.161 | 0.045 |
| 13.77 | 7.077 | 7.119 | 0.042 |
| Average Unit of Difference | | | 0.034 |

Results in Table 6 show $pCO_2$ measurements of samples taken using the AAS/Flex autosampler compared to measurements from manual sampling. Table 6 further demonstrates accurate sampling using the AAS valve of the invention.

TABLE 6

$pCO_2$ Performance of the AAS/Flex Autosampler @ 30 L Scale

| | pH | | |
|---|---|---|---|
| Day | AAS | Manual | % Difference |
| 0.37 | 69.6 | 70.8 | 1.72 |
| 0.82 | 64.7 | 60.4 | 6.65 |
| 1.84 | 43.0 | 35.6 | 17.21 |
| 3.06 | 27.0 | 25.5 | 5.56 |
| 3.40 | 30.7 | 29.1 | 5.21 |
| 3.83 | 36.9 | 31.7 | 14.09 |
| 4.10 | 36.9 | 38.1 | 3.25 |
| 4.41 | 39.6 | 37.8 | 4.55 |
| 4.80 | 42.2 | 40.8 | 3.32 |
| 5.42 | 42.6 | 38.9 | 8.69 |
| 5.80 | 42.5 | 41.6 | 2.12 |
| 6.08 | 42.9 | 41.2 | 3.96 |
| 6.39 | 47.5 | 42.3 | 10.95 |
| 6.80 | 47.5 | 45.9 | 3.37 |
| 7.10 | 48.1 | 47.0 | 2.29 |
| 7.38 | 47.3 | 39.9 | 15.64 |
| 7.86 | 46.8 | 45.8 | 2.14 |
| 8.93 | 48.7 | 42.2 | 13.35 |
| 9.78 | 49.0 | 46.5 | 5.10 |
| 10.11 | 49.6 | 46.8 | 5.65 |
| 10.40 | 51.4 | 48.4 | 5.84 |
| 11.91 | 58.2 | 51.1 | 12.20 |
| 12.70 | 76.7 | 73.7 | 3.91 |
| 13.77 | 95.9 | 88.3 | 7.92 |
| Average % Difference | | | 6.86 |

Results in Table 7 show osmolarity measurements of samples taken using the AAS/Flex autosampler compared to measurements from manual sampling. Table 7 further demonstrates accurate sampling using the AAS valve of the invention.

TABLE 7

Osmolarity Measurement of the AAS/Flex Autosampler @ 30 L Scale pH

| Day | AAS | Manual | % Difference |
|---|---|---|---|
| 0.37 | 351 | 329 | 6.27 |
| 0.82 | 349 | 325 | 6.88 |
| 1.84 | 342 | 306 | 10.53 |
| 3.06 | 348 | 352 | 1.15 |
| 3.4 | 354 | 327 | 7.63 |
| 3.83 | 362 | 341 | 5.80 |
| 4.1 | 366 | 360 | 1.64 |
| 4.41 | 370 | 343 | 7.30 |
| 4.8 | 375 | 374 | 0.27 |
| 5.8 | 379 | 375 | 1.06 |
| 6.08 | 381 | 380 | 0.26 |
| 6.39 | 380 | 356 | 6.32 |
| 6.8 | 383 | 376 | 1.83 |
| 7.1 | 382 | 375 | 1.83 |
| 7.38 | 380 | 350 | 7.89 |
| 7.86 | 385 | 378 | 1.82 |
| 8.93 | 377 | 344 | 8.75 |
| 9.78 | 373 | 377 | 1.07 |
| 10.11 | 375 | 371 | 1.07 |
| 10.40 | 376 | 373 | 0.80 |
| 11.91 | 380 | 383 | 0.79 |
| 13.77 | 388 | 396 | 2.06 |
| Average % Difference | | | 3.77 |

Exemplary Applications of Various Systems and Methods Disclosed Herein

As described herein, optimal production in bioreactors requires regular sampling for off-line analysis to ensure the process remains within the desired operating space for maximum product production. The automated valve disclosed herein, the Automated, Aseptic Sampling (AAS) system can provide rapid, closed-cycle sampling of the bioreactor, steam-in-place (SIP) sterilization between samples, and direct sample delivery to an analyzer. The AAS not only automates and facilitates the sampling process, but can also provide greater reproducibility when compared to manual sampling and has the additional benefits of safety and reliability. The automated sample scheduling and communication with the analytical devices enhances the ability to integrate with process control strategies.

The AAS was installed on 30-L and 130-L bioreactors. Samples were collected using the sampling system and analyzed using a NOVA Flex analyzer (Waltham, Mass.). Outputs from the analyzer included viable cell concentration, cell viability, glucose, pH, partial pressure of carbon dioxide, and osmolality. The AAS system demonstrated the ability to take 3-20× more samples compared to the conventional manual methods typically used, over long periods of time, without affecting the integrity of the bioreactor process. The system performed more consistently and reliably than when samples were taken manually in the development area and showed improved reproducibility.

Some features of the design of the AAS and its sample cycle (as tested in this example) are provided below.

Design

Compact/self-contained with on-board, closed-cycle, sample pump

Current Good Manufacturing Practice (cGMP) compliant

OPC communication capable for integration with variety of analyzers and devices

Unique valve design

Scheduler with operator-specified sampling intervals

Sample Cycle (<45 minutes)

SIP for sterilization

Cool down followed by condensate purge

Sample draw

Sample dispense to sample-handling device or directly to analytical instrument

In tests with the AAS system, more than 500 samples were taken in a four-week-long test; while more than 150 samples were taken in three, two-week-long tests. In all instances, the system performed more consistently and reliably than when samples were taken manually, and the AAS showed improved reproducibility. No system contamination occurred during these tests. During the one testing period, 99 samples were taken without any impact on the sterility of the bioreactor.

The improved performance of the AAS system over manual sampling makes it desirable for use in bioreactors. The AAS demonstrates reliable contamination-free sampling with greater sample consistency and reproduction when compared to manual samples. This scale-independent, low-cost sampling system, which can be manufactured from cGMP-compliant materials, is capable of frequent sampling to enable more intensive process-control schemes. Savings in labor and process optimization/efficiency can be achieved. Moreover, the highly efficient AAS also has use in disposable systems and downstream applications.

The automated sampling systems described herein can advantageously allow for more frequent collection of data, reduce sampling variation and human error associated with the capturing of samples, and reduce costs by reducing labor requirements associated with manual sampling.

It should be understood that the various steps of the disclosed methods and the various components of the disclosed apparatuses are exemplary and the particular order of steps and arrangement of components can be varied without departing from the scope of the invention. For example, FIGS. 26-29 illustrate additional embodiments with various components of the apparatus rearranged, resulting in variations in the order and/or manner in which the steps of the respective methods are performed. These additional embodiments are merely examples of some of the manners in which the steps and/or components of the disclosed embodiments can be rearranged without departing from the scope of the invention. Other rearrangement of steps and/or components are contemplated.

Figure 23:
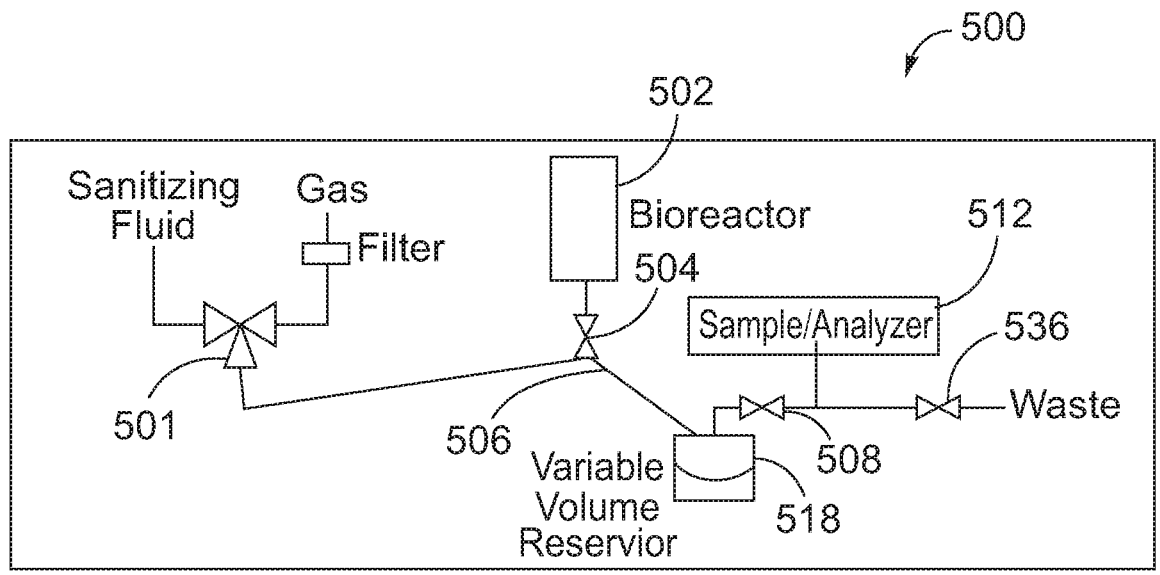
FIG. 23 illustrates a schematic view of an exemplary sampling system for obtaining samples from enclosed containers.

FIG. 23 illustrates an exemplary embodiment of a sampling device 500 in which the introduction of a sanitizing fluid (e.g., steam) and a purge fluid (e.g., air) into a fluid flow path of the apparatus occurs through a common valve device 501 (e.g., a three-way valve device). In this manner, the sanitizing fluid (e.g., steam) and purge fluid (e.g., air) can enter into the fluid flow path 506 at a common location rather than at separate locations as shown, for example, in FIG. 1.

In operation, for example, a sanitizing fluid (e.g., steam) can be delivered into fluid flow path 506 via a three-way valve 501 to clean the path and/or remove any material from previous samples in the area contacted by the sanitizing fluid. After the sanitizing step, a purge fluid (e.g., air) can be delivered to the fluid flow path 506 via the same valve 501. Because valve 501 is upstream of sample collection valve 504 (which is, in turn, coupled to the bioreactor 502), the air can eliminate and/or reduce the amount of sanitizing fluid remaining within fluid flow path 506 after fluid flow path 506 is exposed to the sanitizing fluid. Thus, three-way valve 501 is operable between a first position that restricts the flow of air (or other purging fluid) but permits sanitizing fluid to pass through, a second position that permits the flow of air (or other purging fluid) and restricts the passage of sanitizing fluid, and a third position that restricts the flow of both air (or other purging fluid) and the sanitizing fluid.

The remaining operation of the device illustrated in FIG. 23 can be generally similar to that described elsewhere herein. For example, a variable volume reservoir 518 can draw a sample from bioreactor 502 through an open sample collection valve 504. The variable volume reservoir 518 can comprise, for example, a diaphragm pump as described elsewhere herein. After the sample is drawn into variable volume reservoir 518, it can be discharged through outlet valve 508 to be captured for analysis and/or further processing by an analyzer 512. To facilitate delivery of the sample to the analyzer 512, a control valve 536 can be provided downstream of outlet valve 508. As described elsewhere herein, a control valve 536 can be provided to open and close to allow and restrict the discharge of fluids to a waste collection area. The discharged waste can include, for example, sanitizing fluid and purging gas that has traveled along fluid flow path 506 to sanitize and purge excess sample materials from fluid flow path 506.

Figure 24:
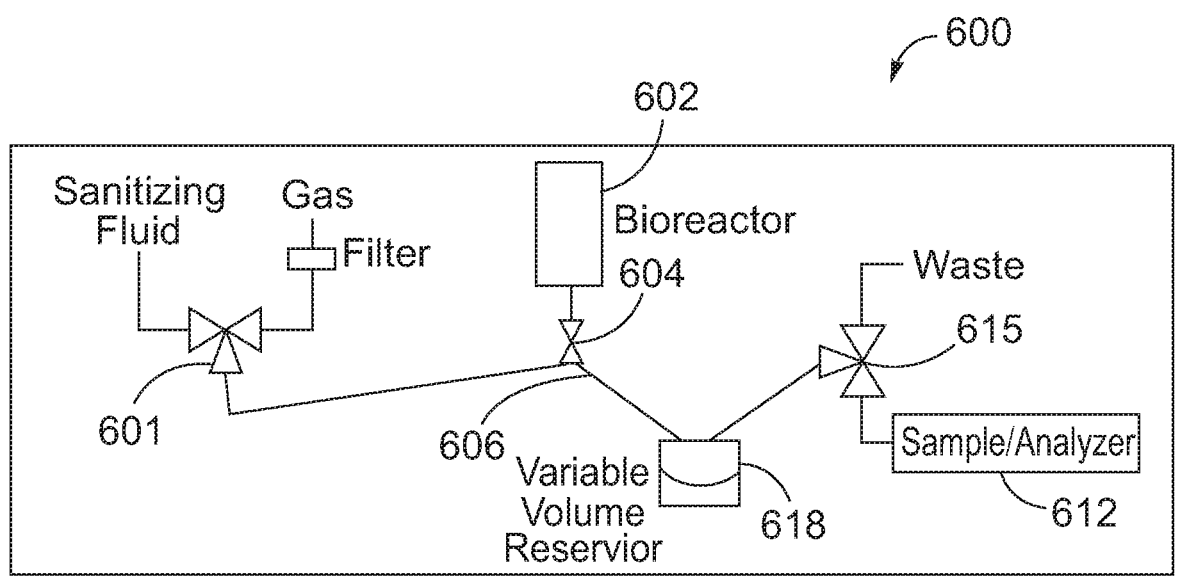
FIG. 24 illustrates a schematic view of an exemplary sampling system for obtaining samples from enclosed containers.

FIG. 24 illustrates another exemplary embodiment of a sampling device 600. In this embodiment, the sanitizing fluid (e.g., steam) and purge fluid (e.g., air) are also configured to be delivered into a fluid flow path 606 at a common location (e.g., via a three-way valve 601) as described in FIG. 23. FIG. 24, however, illustrates an alternative embodiment in which the components and steps downstream from the sample inlet valve are arranged differently from other embodiments disclosed herein.

As shown in FIG. 24, a sample collection valve 604 is coupled to a bioreactor 602 and a variable volume reservoir 618 is provided downstream of the sample collection valve 604. A three-way valve 615 is provided downstream from variable volume reservoir 618, with valve 615 being configured to permit delivery of a sample and/or other materials in fluid flow path 606 through valve 615 to an analyzer 612 or, alternatively, to a waste collection area. Accordingly, when capturing a sample, the system draws the sample into variable volume reservoir 618 and valve 615 moves to a first configuration which permits the delivery of the sample through valve 615 to analyzer 612. After sample collection, valve 615 moves to a second configuration which restricts fluid flow to analyzer 612 and permits fluids in the flow path 606 (e.g., sanitizing fluid and purging gas) to be directed to a waste collection area.

Figure 25:
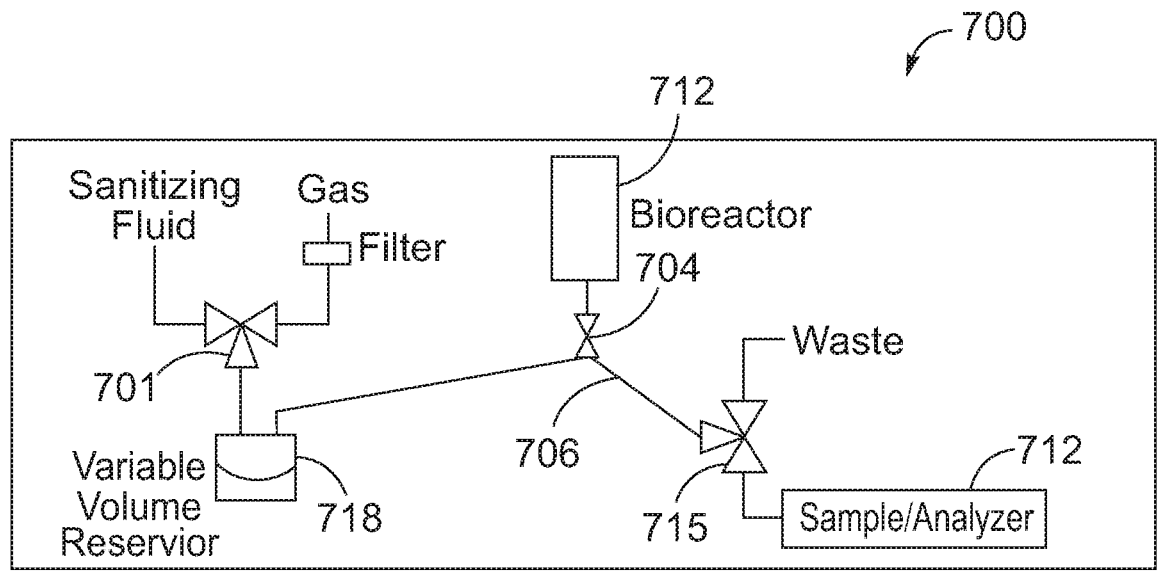
FIG. 25 illustrates a schematic view of an exemplary sampling system for obtaining samples from enclosed containers.

FIG. 25 illustrates another exemplary sampling apparatus 700. Apparatus 700 comprises a three-way valve 701 and a bioreactor 702 coupled to a sample collection valve 704. Unlike other embodiments disclosed herein, a variable volume reservoir 718 can draw a sample "upstream" through sample collection valve 704. Once the sample is drawn, the sample collection valve 704 can close and the variable volume reservoir 718 can discharge the sample back "downstream" along fluid flow path 706 towards a three-way valve 715 that is provided downstream from variable volume reservoir 718. Valve 715, can be configured to permit delivery of the sample and/or other materials in the fluid flow path 706 through valve 715 to an analyzer 712 or to discharge as waste. Accordingly, when capturing a sample, the system draws the sample "upstream" into variable volume reservoir 718 and variable volume reservoir 718 then delivers the sample through valve 715 to analyzer 712. After sample collection and discharge to analyzer 712, valve 715 can restrict fluid flow to analyzer 712 and instead direct fluids in the flow path 706 (e.g., sanitizing fluid and purging gas) through valve 715 to a different path for waste collection.

Figure 26:
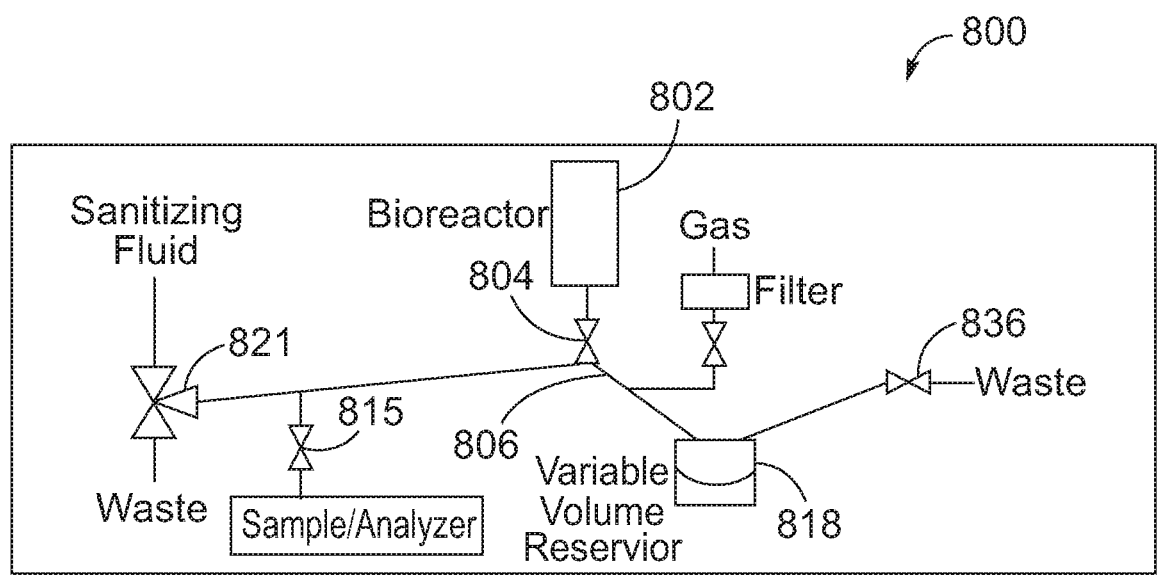
FIG. 26 illustrates a schematic view of an exemplary sampling system for obtaining samples from enclosed containers.

FIG. 26 illustrates another exemplary sampling apparatus 800. As in other systems described herein, apparatus 800 comprises a bioreactor 802 coupled to a sample collection valve 804. Other components of apparatus 800, however, are rearranged to operate somewhat differently from other systems described herein. For example, although the sanitizing fluid inlet is positioned upstream (e.g., at three-way valve 821) of sample collection valve 804, a purging fluid inlet is positioned downstream of sample collection valve 804. In operation, variable volume reservoir 818 can draw a sample "downstream" through sample collection valve 804. Once the sample is drawn, sample collection valve 804 can close and the variable volume reservoir 818 can deliver the sample "upstream" along fluid flow path 806 towards three-way valve 821. Valve 815 can be configured to permit delivery of the sample through valve 815 to analyzer 812. Thus, when capturing a sample, the system draws the sample "downstream" into variable volume reservoir 818 and variable volume reservoir 818 then delivers the sample back "upstream" through valve 815 to analyzer 812. After sample collection and delivery to analyzer 812, valve 815 is closed so that sanitizing fluid can be delivered through valve 821 and along fluid flow path 806 to sanitize fluid flow path 806. After sanitization, a purge fluid (e.g., air) can be delivered into the fluid flow path 806 (as shown in FIG. 26) and valve 821 can be directed to waste, and control valve 836 can be opened to allow discharge of fluids in the flow path 806 (e.g., sanitizing fluid and purging gas) for waste collection.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. An aseptic automatic fluid sampling system, comprising:
   a variable volume reservoir, wherein the variable volume reservoir comprises diaphragm pump, moveable between a first configuration that defines a first volume for receiving a fluid sample from a container and a second configuration that defines a second volume, the first volume being larger than the second volume, the variable volume reservoir comprising a variable volume reservoir inlet through which the fluid sample is received into the variable volume reservoir, and a variable volume reservoir outlet through which the fluid sample is discharged from the variable volume reservoir;
   a sample collection valve moveable between an open configuration and a closed configuration, the sample collection valve being coupled to a fluid outlet of the container;
   a sample delivery flow path beginning at the sample collection valve and extending downstream to the inlet of the variable volume reservoir, the sample collection valve being in fluid connection with the inlet of the variable volume reservoir when the sample collection valve is in the open configuration;

a three-way valve upstream of the sample collection valve, the three-way valve being operable at a first position that permits the flow of a sanitizing fluid through the three-way valve, the three-way valve being operable at a second position that permits the flow of a purge fluid through the three-way valve, forming a purge fluid delivery flow path; and the three-way valve being operable at a third position that restricts the flow of both the sanitizing fluid and of the purge fluid through the three-way valve;

the three-way valve being positioned to receive the sanitizing fluid from a sanitizing fluid source separate from the container;

an outlet valve positioned downstream of the variable volume reservoir outlet, the outlet valve being moveable between an open configuration and a closed configuration; wherein the sample collection valve is upstream of the variable volume reservoir; and a sanitizing fluid flow path beginning at the three-way valve and extending downstream at least between the three-way valve and the inlet of the variable volume reservoir, the sanitizing fluid flow path completely overlapping the sample delivery flow path, wherein movement of the variable volume reservoir from the first configuration to the second configuration causes the fluid sample to be drawn aseptically and discharged from the variable volume reservoir, and wherein, when the sample collection valve is in the closed configuration and the three-way valve is in the first position, the sanitizing fluid flow path extends downstream at least from the three-way valve to the sample collection valve and from the sample collection valve to the inlet of the variable volume reservoir, and the sample collection valve is in fluid connection with the inlet of the variable volume reservoir so the sample delivery flow path may be sanitized frequently.

2. The aseptic automatic fluid sampling system of claim 1, wherein, when the sample collection valve is in the closed configuration and the three-way valve is in the second position, the purge fluid delivery flow path extends at least from the three-way valve to the sample collection valve and from the sample collection valve to the variable volume reservoir.

3. The aseptic automatic fluid sampling system of claim 1, further comprising a control valve positioned downstream of the outlet valve.

4. The aseptic automatic fluid sampling system of claim 3, wherein the control valve comprises a variable back-pressure regulator.

5. The aseptic automatic fluid sampling system of claim 3, wherein the control valve comprises a thermostatically-controlled valve.

6. The aseptic automatic fluid sampling system of claim 1, wherein the variable volume reservoir comprises a flexible diaphragm member and a housing with a first area and a second area, the flexible diaphragm member being configured to move between a first position where a first surface of the flexible diaphragm member contacts the first area of the housing and a second position where a second surface of the flexible diaphragm member contacts the second area of the housing.

7. The aseptic automatic fluid sampling system of claim 6, wherein the first surface of the flexible diaphragm member is generally opposite the second surface of the flexible diaphragm member.

8. The aseptic automatic fluid sampling system of claim 6, wherein the flexible diaphragm member comprises a generally spherical housing and the first area is a first half of the generally spherical housing and the second area is a second half of the generally spherical housing, wherein the second surface contacts the second half of the generally spherical housing when in the second position, the flexible diaphragm member being generally inverted when in the second position, relative to its orientation when in the first position.

9. The aseptic automatic fluid sampling system of claim 1, wherein the sample collection valve comprises a valve stem with a tapered sealing member that moves from a first position when the sample collection valve is in the open configuration to a second position when the sample collection valve is in the closed configuration, wherein a portion of the valve stem extends into the sanitizing fluid flow path when the sample collection valve is in the second position.

10. The aseptic automatic fluid sampling system of claim 1, wherein the sample collection valve, and the three-way valve are contained within a single housing.

* * * * *